United States Patent [19]
Clark, Jr. et al.

[11] Patent Number: 5,530,193
[45] Date of Patent: Jun. 25, 1996

[54] MAIZE DWARF MOSAIC VIRUS RESISTANT PLANTS

[76] Inventors: John M. Clark, Jr., 909 E. Sunnycrest, Urbana, Ill. 61801; Joseph Jilka, 2242 Village Green Pkwy. 190 7, Chesterfield, Mo. 63017; Lynn E. Murry, 1124 Los Trancos, Portola Valley, Calif. 94025; Liliana E. C. Scarafia, 1031 Varsity Ct., Mountain View, Calif. 94040

[21] Appl. No.: 229,287

[22] Filed: Apr. 18, 1994

Related U.S. Application Data

[63] Continuation of Ser. No. 67,257, May 25, 1993, abandoned, which is a continuation of Ser. No. 817,922, Jan. 8, 1992, abandoned.

[51] Int. Cl.⁶ .............................. A01H 5/00; A01H 5/10; C12N 15/40; C12N 15/82
[52] U.S. Cl. ................. 800/205; 800/250; 800/DIG. 56; 435/69.1; 435/70.1; 435/172.3; 536/23.72
[58] Field of Search ........................ 536/23.72; 800/205, 800/250, DIG. 56; 435/69.1, 70.1, 172.3, 240.4, 320.1, 235.1

[56] References Cited

FOREIGN PATENT DOCUMENTS

| | | | |
|---|---|---|---|
| 223452 | 10/1986 | European Pat. Off. | ........ C12N 15/00 |
| 9115587 | 10/1991 | WIPO | ............................ C12N 15/40 |

OTHER PUBLICATIONS

Berger et al. "Properties and in vitro Translation of Maize Dwarf Mosaic Virus RNA" J. Gen. Virol. (1989) v 70, pp. 1845–1851.

Mikel et al. "Genetics of resistance of 2 dent corn inbreds to maize dwarf virus . . . " Biological Abstracts, v 78, (1984), abstract No. 38535.

Shukla et al. "Present status of the sugarcane mosaic subgroup of potyviruses" Arch. Virol. Suppl. v 5, (1992), pp. 363–373.

Fenkel et al. Journal of General Virology, vol. 72, part 2 pp. 237–242 (1991).

Beachy et al. "Coart Protein-Mediated Resistance Against Virus Infection" Annu. Rev. Phytopath. (1990) 23:451–74.

Ling et al. "Protection Against Detrimental Effects of Potyvirus Infection In Transgenic Tobacco" Bio/Technology (1991) 9:752–758.

Stark, et al. "Protection Against Potyvirus Infection in Transgenic Plants" Bio/technology (1989) 7:1257–1262.

Powell, et al. "Protection Against Tobacco Mosaic Virus Infection In Transgenic Plants" Virology (1990) 175:124–130.

Jensen, et al. "Factors Influencing Virus Titer in Maize Dwarf Mosaic Virus–Infected Sorghum" Phytopathology (1985) vol. 75 10:1132–1136.

Raymond Louie "Effects of Genotype and Inoculation Protocols on Resistance Evaluation of Maize" Phytopathology (1986) vol. 76 8:769–773.

Tosic et al. "Differentiation of Sugarcane, Maize Dwarf, Johnsongrass and Sorghum Mosaic Viruses" Plant Disease (1990) vol. 74 8:549–552.

McMullen et al. "The Linkage of Molecular Markers to a Gene Controlling the Symptom Response" Molecular Plant–Microbe Interactions (1989) vol. 2 6:309–314.

Pirone "Sugarcane Mosaic Virus" C.M.I./A.A.B. Descriptions of Plant Viruses (1972) 88.

Potrykus, I. 1990. Bio/Technology vol. 8, No. 6, pp. 535–542.

McKern, N. M. et al. 1990. Phytopathology vol. 80 No. 10 pp. 907–912.

Suggs, S. V. et al. 1981. Proc. Natl. Acad. Sci. USA vol. 78 No. 11 pp. 6613–6617.

Nejidat et al. 1990. Physiol. Plant. 80: 662–668.

Jilka et al. 1988. Phytopathology 78(12): 1598.

Jilka et al. 1991. Dissertation Abstracts International 51(12): 5719.

Eggenberger et al. 1989. J. Gen. Virol. 70:1853–1860.

Gordon-Kamm et al. 1990. Plant Cell 2: 603–618.

Callis et al. 1987. Genes & Devel. 1: 1183–1200.

Primary Examiner—David T. Fox
Attorney, Agent, or Firm—Allen E. Norris; Lynn Marcus-Wyner

[57] ABSTRACT

Plants are transformed with the coat protein gene of one of various strains of Maize Dwarf Mosaic Virus (MDHV), and are protected from serious disease when challenged with exposure to the virus. The nucleic acid and amino acid sequences of MDMV strains A, B, and KS1 are given, as well as the constructs and vectors used to produce the transformed plants.

9 Claims, 9 Drawing Sheets

MAIZE DWARF MOSAIC VIRUS RESISTANT PLANTS

This is a continuation of application Ser. No. 08/067,257, filed on May 25, 1993, now abandoned, which is a continuation of application Ser. No. 07/817,922, filed on Jan. 8, 1992, now abandoned.

This invention relates to plants which have reduced susceptibility to various strains of Maize Dwarf Mosaic Virus (MDMV), the nucleotide and amino acid sequences of the MDMV vital coat proteins, use of these sequences to produce transgenic plants, and the vectors used to transform the plants.

BACKGROUND OF THE INVENTION

It has been observed that when a plant is transformed with a gene encoding a viral coat protein (CP), the resulting transgenic plant is often less susceptible or resistant to infection by that same virus. This phenomenon has been referred to as "coat protein-mediated resistance" (See Beachy et al, 1990 *Annu. Rev. Phytopathol.* 28:451–74 for a review). In some cases, the transgenic plants may also be less susceptible or resistant to viruses which are related to the virus which was the source of the CP gene, but remain susceptible to viruses which are not related.

The potyviruses make up one of the largest groups of plant viruses, and these viruses are responsible for damage to many of the world's major crops. A potyvirus has a (+)sense RNA genome which is usually about 10 kb in length. This is translated into a single polyprotein which is later cleaved and processed into various proteins, including replicases, proteases, movement proteins, and a coat protein. Stark et al., 1989, *Bio/Technol.* 7:1257–1262 succeeded in producing transgenic tobacco plants which expressed various levels of the CP of a polyvirus, soybean mosaic virus (SMV). The transgenic tobacco plants were challenged with other viruses, including two potyviruses, potato virus Y (PVY) and tobacco etch virus (TEV). It was found that the plants were protected against PVY and TEV, but not unrelated viruses. As SMV, PVY, and TEV show relatively low amino acid homologies, it was concluded that CP-mediated resistance requires some structural as well as some sequence homology.

One of the major vital diseases of corn (*Zea mays*) is caused by a potyvirus, maize dwarf mosaic virus (MDMV). MDMV occurs throughout the midwestern U.S. corn belt. Symptoms include the appearance of faint yellow stripes on plants 6–7 weeks old and shortened internodes. Eventually, the yellowing leaves may turn purplish or become necrotic. The mature plant may tiller excessively and bear grainless ears. Annual losses due to MDMV infections alone are estimated between 2–10% annual yield. However, if MDMV-A is present in a mixed infection with Maize Chlorotic Dwarf Virus, yields can be decreased by 50%, and a mixed infection of MDMV-B and Maize Chlorotic Mottle Virus, can result in a 100% loss. While one source of genetic resistance to MDMVs has been observed in some lines, such as MDM-1 (McMullen et al. 1989 *Mol. Plant-Microbe Interact.* 2(6):309–314), the mechanisms promoting the resistance (and their underlying basis) are not well understood.

It would be desirable to identify other genes or introduce numerous sources of resistance into a wide variety of corn plants to protect against the inevitable evolution of the Maize Dwarf Mosaic Virus complex.

DESCRIPTION OF THE INVENTION

This invention includes the nucleotide sequence of the coat proteins (CP) of various strains of MDMV and functional equivalents thereof, their use in producing Transgenic plants which express a CP of one of these MDMVs, to vectors used in producing the transgenic plants, and the transgenic plants so produced.

There are numerous strains of potyviruses. Their taxonomy is complex, as they have been generally named for the host on which they have been isolated. In accordance with this invention, the coat protein genes of three potyviruses are given: Maize Dwarf Mosaic Virus strain A (MDMV-A), Maize Dwarf Mosaic Virus strain B (MDMV-B) (also known as Sugarcane Mosaic Virus), and Maize Dwarf Mosaic Virus strain KS-1 (MDMV-KS1). The nucleotide and deduced amino acid sequences for each of these viruses is presented in the accompanying Table 1 (MDMV-A) (SEQ. ID. NO. 1 and SEQ. ID. NO. 2), Table 2 (MDMV-B) (SEQ. ID. NO. 3 and SEQ. ID. NO. 4), and Table 3 (MDMV-KS1) (SEQ. ID. NO. 5 and SEQ. ID. NO. 6).

The transgenic plants are made as follows. First, for each of the MDMV strains, the MDMV viral RNA is isolated. The vital genomes are found to include numerous regions, similar to those of other potyviruses, including: a) a nuclear inclusion protein II, the vital capsid (coat) protein, a 3'-untranslated region, and a polyadenylated 3'-terminus. A cDNA clone which has a fragment corresponding to the capsid protein is isolated and .the capsid protein gene is sequenced. An expression cassette comprising a CP gene, operatively ligated to a promoter which functions in a plant cell, along with additional sequences desirable for optimal expression, such as introns and untranslated leader sequences (see, for example, Dietrich et al 1987 *J. Cell Biol.* 105:245a; and Mascarenhas et al 1990 *Plant Mol. Biol.* 15:913–920) is constructed and placed into a cloning vector. Plant cells are transformed and transgenic plants are regenerated from cell culture.

Homology studies have shown that in potyvirus coat proteins there is a consistently homologous amino acid sequence, Trp-Cys-Ile-Glu-Asn (SEQ. ID. NO. 7). See, for example, Lain et al, 1988 *Virus Research* 10:325–342, where this sequence appears at positions 181–185. Heterologous (mixed) deoxyoligonucleotide primer-probes complementary to mRNA sequences that would code for this sequence were prepared and used to prime single stranded DNA synthesis from the MDHV-RNAs in the presence of various dideoxynucleoside-5'-triphosphates. This resulted in a single stranded cDNA sequence complementary to the MDHVRNA coding for a portion of the CP. Using this cDNA sequence, a homogeneous deoxynucleotide primer-probe was synthesized which was exactly complementary to 25 nucleotides of the M/)HV RNA coding for CP.

It has been observed that potyviruses typically have 3'-terminal poly A regions. Therefore, oligo(dT)$_{22}$ was used to prime double stranded cDNA synthesis from HDH-VRNA. cDNAs approximately 1000–8000 bp in length (averaging 5000) were thus obtained and then separately digested with different restriction endonucleases. The resultant cDNA fragments were separated by gel electrophoresis, and cDNAs which met the following criteria were identified: 1) able to hybridize with 5'-$^{32}$P oligo (dT)$_{22}$, i.e derived from the 3'-terminal region of MDMV RNA; 2) able to hydridize with the 5'-$^{32}$P homogeneous deoxyoligonucleotide primter-probe, i.e. contained cDNA from MDHV RNA which coded for MDHV CP; and 3) were greater than 1300 base pairs, i.e. were long enough to include cDNA from a large enough portion of the 3' terminus of MDHV RNA to encompass the MDMV DP gene.

For MDMV-B, an approximately 1600 bp cDNA fragment released from the double stranded cDNA by digestion with HindIII met all the above criteria, and dictated that this cDNA contained a HindIII site .approximately 1600 bp from the cDNA region complementary to the 3'-terminal poly A region of MDMV-B RNA. Using this information about the HindIII site, double stranded cDNA from the 3' terminus of MDMV-B was cloned into the HindIII to EcoRI region of plasmid pUC19. Plasmids containing the desired cDNA insert are then detected by their ability to hybridize with the 5'-$^{32}$P homogeneous deoxyoltgonucleotide primer-probe.

The native CP gene does not contain a ATG start codon, therefore the cDNA sequence is preferably modified to include this. Also, other modifications to the nucleic acid sequence (not affecting the amino acid sequence) are preferably made to facilitate plasmid manipulations, and polylinkers may also be added. The modified genes are operably linked to a promoter which is functional in plant cell, such as a Cauliflower Mosaic Virus 35S promoter (such as described by any of: Gardner et al, 1981, *Nucl. Acids Res.* 9:2871–2888; Franck et al, 1980 *Cell* 21:285–294; or Gallie et al, 1988 *Nucl. Acids Res.* 16:883–893), and an intron (such as those described by Mascarenhas et al, 1991 *Plant Mol. Biol.* 15:913–920). The plasmids are introduced into cells or protoplasts using known techniques (such as electropotation or particle bombardment), and if desired, the cells or protoplasts may be co-transformation with a second plasmid carrying a plant marker gene. Transformed cells are regenerated into calli, and then plants. The plants are tested and are shown to express the CP gene, and are seen to have increased resistance to MDMV infection compared to their non-transformed counterparts.

Figure 1:
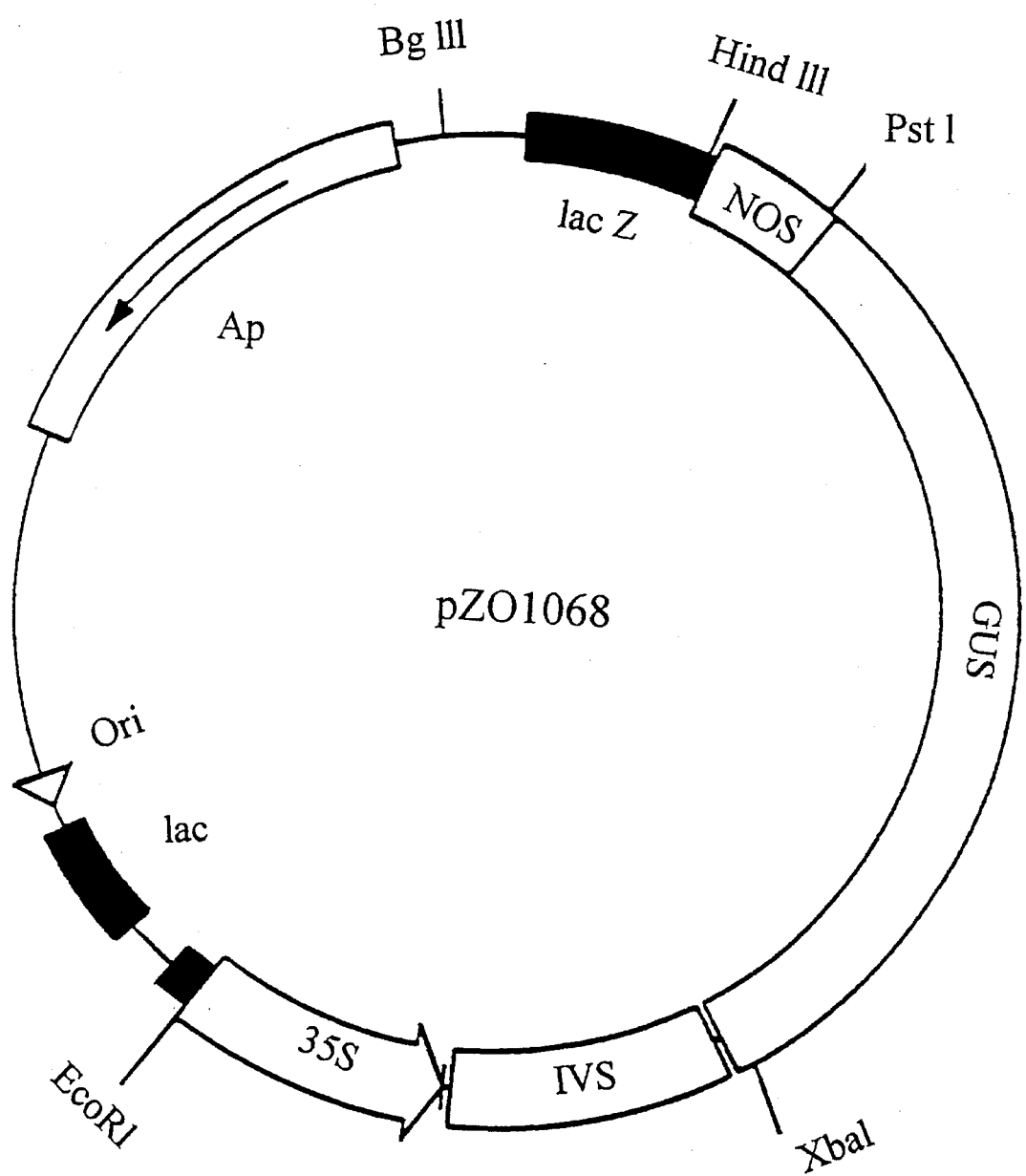
FIG. 1 is a map of the plant expression vector pZO1068.

As used throughout the specification and claims the following definitions apply:

Stringent hybridization conditions—those in which hybridization is effected in a standard manner at 65° C. in 4X buffered saline (a.k.a. SSPE buffer) followed by washing at 52° C. in 0.2 X SSPE, which will not affect true hybrids which have formed.

Resistant—Plants which when challenged with a virus show either no symptoms or symptoms which are mild enough so that there are no substantial economic consequences.

Tolerant—Plants which when challenged with a virus experience either 1) milder symptoms than a susceptible plant, or 2) delayed onset of symptoms, or 3) experiences symptoms, but are able to compartmentalize the symptoms (so that only a portion of the plant is affected), outgrow the symptoms, overcome, or neutralize the symptoms. Yield may be reduced somewhat compared to the same plant grown in the absence of MDMV, but is increased compared to an infected susceptible plant.

Susceptible—Plants which show symptoms which are severe enough to cause economic damage, for example, a 10% or greater decreased yield than is otherwise expected for that plant.

Functional Equivalent of a MDMV coat protein—A protein which is substantially similar in three-dimensional structure to the naturally occurring CP of MDMV-A, MDMV-B or MDMV-KS1, such that is confers protection from at least one of the aforementioned strains equivalent to that conferred by the naturally occurring CP.

The plants which may be transformed in accordance with this invention may be any plant desired. While plants which are normally susceptible to MDMV infection, such as susceptible members of the family Graminea, and more particularly, susceptible corn plants, are preferred, this invention also encompasses transforming plants which exhibit a higher level of tolerance or resistance in order to develop a wider base of resistant germplasm, develop model systems, or study the CP mediated-resistance phenomenon.

The CP sequence used to transform the desired plant may be any DNA sequence which codes for the same amino acids as one of the RNA sequences given in Tables 1–3. It is preferred that the CP sequence will hybridize under stringent hybridization conditions to a cDNA sequence which corresponds to any of the RNA sequences of Tables 1–3. It is recognized that minor changes in the amino acid sequence (either by substitution, addition, or deletion) will often result in a peptide which has the same protective properties as the natural coat protein. As it has been observed in other potyviruses that the structural conformation of the protein plays a role in conferring protection, it is particularly preferred that any modification to the amino acid sequence does not substantially alter the three-dimensional structure of the coat protein. Therefore, amino acids which are known to contribute extensively to the three-dimensional configuration (through cross-linking or otherwise) such as cysteine, should preferably not be altered. Thus, another aspect of this invention is transforming a plant with a DNA sequence which encodes a protein which is substantially similar in three-dimensional structure to the naturally occurring coat protein of MDMV-A, MDMV-B or MDMV-KS1, such that it confers protection from at least one of the aforementioned strains equivalent to that conferred by the naturally occurring CP.

The following non-limiting Examples are presented to better illustrate the invention.

EXAMPLE 1

Isolation of MDMV-B

The Iowa isolate of MDMV-B (ATCC-PV$_{53}$) is grown in 2 week old "Gold Cup" sweet corn seedlings. All the following isolation steps are at 46° C. Three weeks after inoculation, 100 g of infected corn leaves are homogenized for 2 minutes in a Waring blender with 200 ml 0.1 M sodium borate buffer, pH 7.8, 0.01 M Na$_2$EDTA, 0.01 M sodium diethyldithiocarbamic acid mixed with 25 ml CHCl$_3$ and 25 ml CCl$_4$. The resulting suspension is clarified by centrifugation at 8,000×g for 10 minutes and the aqueous phase is decanted through two layers of cheesecloth. Triton X-100 is added to the aqueous phase to a concentration of 5% (v/v) and this solution is stirred for 30 minutes and further clarified by centrifugation hat 8,000×g for 10 minutes and then is decanted. The resulting supernate is centrifuged at 105,000×g for 2 hours and the pelleted crude MDMV-B is allowed to solubilize by gently shaking in 10 ml of 0.05 M sodium borate, pH 7.8 for 8–16 hours. The solubilized KDMV-B is clarified by centrifugation at 8,000×g for 10 minutes and the resultant insoluble material is further solubilized in 10 ml of 0.05 M sodium borate, pH 7.8 as before, and then is reclarified by centrifugation (8,000×g for 10 minutes). The 20 ml of combined crude MDMV-B is layered onto two 5 ml pads of 60% sucrose containing 6% (W/V) cesium sulfate. These samples are then centrifuged at 134,000×g for 18 hours in a swinging bucket rotor (Beckman SW41) and then the optically dense band of the virus in the sucrose-Cs$_2$SO$_4$ pad is collected, mixed with 8–10 volumes of 0.05 M sodium borate, pH 7.8, and finally sedimented by centrifugation at 330,000×g for 1 hour. The final pellets of MDMV-B are solubilized overnight by gentle shaking in a total of 2 ml of 0.05 M sodium borate, pH 7.8 and stored until used.

EXAMPLE 2

Isolation of MDHV-B RNA

All water used to make solutions in the following procedures is made as 0.1% diethylpyrocarbonate and then is autoclaved prior to use. MDMV-B RNA is isolated according to Hellman et al. 1980, *Virology* 106:207–216, which is hereby incorporated by reference, except that the sucrose gradients contain 0.01 M Tris-Cl, pH 7.4, 0.001 H Na$_2$EDTA, 0.5I sodium dodecyl sulfate, and 0.1 mg/ml bentonite. The resultant MDMV-B RNA solution is mixed with 1/30 volume of 3H sodium acetate, pH 6, and then the MDMV-B RNA is precipitated with 2 volumes of ethanol. This MDMV-B RNA is then purified further on an oligo(dT) column as specified by the manufacturer, BRL.

EXAMPLE 3 cDNA Syntheses and Cloning Procedures

Single stranded cDNA is synthesized from MDMV-B RNA using arian myeloblastosis virus reverse transcriptase, various dideoxynucleoside-5'-triphosphates, and a heterogeneous deoxyoligonucleotide primer-probe that is complementary the mRNA sequences coding for the peptide Trp-Cys-Ile-Glu-Asn (SEQ. ID. NO. 7). Double stranded cDNA (ds cDNA) is synthesized from the 3'-terminus of MDMV-B RNA using oligo(dT)$_{22}$ to prime first strand cDNA synthesis, followed by the use of RNase H and subsequent DNA polymerase I catalyzed second strand cDNA synthesis. When appropriate, these reactions contained α$^{32}$P-dCTP to label the ds DNA. labelled and unlabelled ds cDNAs are exhaustively digested with various restriction enzymes, then denatured by 5 minutes of boiling in 0.05 M NaOH, 0.005 M Na$_2$EDTA, and the resultant cDNA fragments are finally resolved by agarose gel electrophoresis. The sizes of fragments released are analyzed by radioautography of the gel resolved $^{32}$P-labelled fragments released from the $^{32}$P-labelled ds cDNAs. cDNA fragments derived from the 3'-terminal region of the MDMV-B RNA are identified by hybridization analyses of unlabelled cDNA fragments using 5'-$^{32}$P-oligo(dT)$_{22}$, oligo(dT)$_{22}$, or a homogeneous 5'-$^{32}$P-deoxyoligonucleotide derived from single strand cDNA nucleotide sequence analysis as hybridization probes.

A modification of the Okayama-Berg procedure (Okayama et al., 1982 *Mol. Cell. Biol.* 2:161–170 is used to construct the ds cDNA clone of the 3'-terminal region of MDMV-B RNA. Specifically, 1 μg of oligo(dT) column purified MDMV-B RNA is incubated with 1 μg of the commercially available vector pUC19 previously linearized by treatment with KpuI, then modified by 3'-terminal T addition, and finally treated with BamHI. A small aliquot of this reaction mix is removed and incubated with 5 μCi of α$^{32}$P-dCTP in order to form $^{32}$P-labelled cDNA as an indicator of the cDNA synthesis. After the second strand cDNA syntheses are completed, the reaction containing α$^{32}$P-dCTP is mixed with the unlabelled reaction and the combined reactions are heated at 65° C. for 5 minutes to terminate cDNA synthesis. The cDNA pUC19 vector is then iso-lated by extraction with phenol:CHCl$_3$ (24:1), centrifugation resolution, aspiration of the aqueous phase, two extractions of the aqueous phase with equal volumes of ether, and precipitation of the cDNA vector by addition of 1 volume of 4M -ammonium acetate and 4 volumes of ethanol. The precipitated cDNA vector is taken up in 20 μl of BRL's "REact 2 buffer" containing 20 units of HindIII and incubated for 3 hours at 37° C. before reisolation of the cDNA vector by extraction with phenol: CHCl$_3$ (24:1) and ether followed by alcohol precipitation as described above. The cDNA vector is then further digested with 20 units of BamHI and reisolated in a manner identical to that of the HindIII treatment above in order to remove any incompletely prepared pUC19 cDNA vector. The now-modified cDNA vector is purified by passage over a 20 cm×1 cm Sepharose CL-4B column in the presence of 0.05 M NH$_4$HCO$_3$, pH 8.0. Fractions containing the first half of the cDNA vector (identified by Cerenkov counting of $^{32}$P) are pooled and lyophilized to dryness. This material is then taken up in, and lyophilized from, four successive 100 μl of H$_2$O, to remove residual NH$_4$HCO$_3$ prior to the final stabilization in 20 μl of H$_2$O, mixing with 1/30 volume of 3 M sodium acetate, pH 6.0, and precipitation with 2 volumes of ethanol. The pelleted cDNA vector is washed by resuspension in, and centrifugation from, 50 μl of 70% ethanol and then lyophilized to dryness. The dried material is redissolved in 50 μl of H$_2$O and then reprecipitated with ethanol, washed in 70% ethanol, and is lyophilized as before. This cDNA vector is dissolved in 20 μl of BRL "ligase reaction mix" and allowed to ligate overnight at 8° C. in the presence of 5 units of DNA ligase prior to dilution with 100 μl of 0.1 M CaCl$_2$. Aliquots of this are used to transform competent *E. coli* TB-1 cells.

Transformed *E. coli* cells are detected by hybridization analysis which employs a homogeneous deoxyoligonucleotide primer-probe derived from sequence analysis of single stranded cDNA synthesized from the hererogenous primer-probe as above. The nucleotide sequence of a single cDNA clone of the 3'-terminal region of MDMV-B RNA is determined by the dideoxynucleotide chain termination method using specific primers.

EXAMPLE 4

Isolation and Sequencing of MDMV-A and MDMV-KS1 CP genes

The procedures of Examples 1–3 are essentially repeated except that the vital isolates are MDMV-A and MDMV-KS1, except that the cDNA containing vectors are circularized by blunt-end ligation (i.e,, the HindIII step is deleted).

EXAMPLE 5

Transformation of Corn Protoplasts

Construction of Expression Vectors Various constructs containing the MDMV-B coat protein gene are made and used to transform corn cells as described below. First, MDMT-B cDNA is modified to include a KpnI restriction site. The KpnI site which is introduced into the second and third codon, does not affect the amino acid sequence, nor does it detrimentally affect codon preferences used by monocots (see Murray et al, 1989 Nucl. Acids Res. 17(2):477–491). Thus the wild type sequence of MDMV-B is

| CAG | TCG | GGA | ACT | SEQ. ID. NO. 8 |
|-----|-----|-----|-----|----------------|
| Gln | Ser | Gly | Thr | SEQ. ID. NO. 9 | where Gln is the last amino acid of the inclusion body protein and Ser is the first amino acid of the coat protein. The mutated sequence with the KpnI site (MDMV-B-Kpn) is

| CAG | TCG | GGT | ACC | SEQ. ID. NO.: 10 |
|-----|-----|-----|-----|------------------|
| Gln | Ser | Gly | Thr | SEQ. ID. NO.: 11 |

MDMV-B-Kpn is modified at the 3' end in order to add a PstI site near the existing SpeI site. To accomplish this, a single self-complementary oligonucleotide is synthesized, LSO3MVAA (C TAG TCT GCA GA; SEQ. ID. NO. 12).

The MDMV-B-Kpn DNA is restricted with SpeI and then ligated to unkinased LSO3MVAA, and inserted into pUC18. The resulting plasmid is pZO1204.

Figure 2:
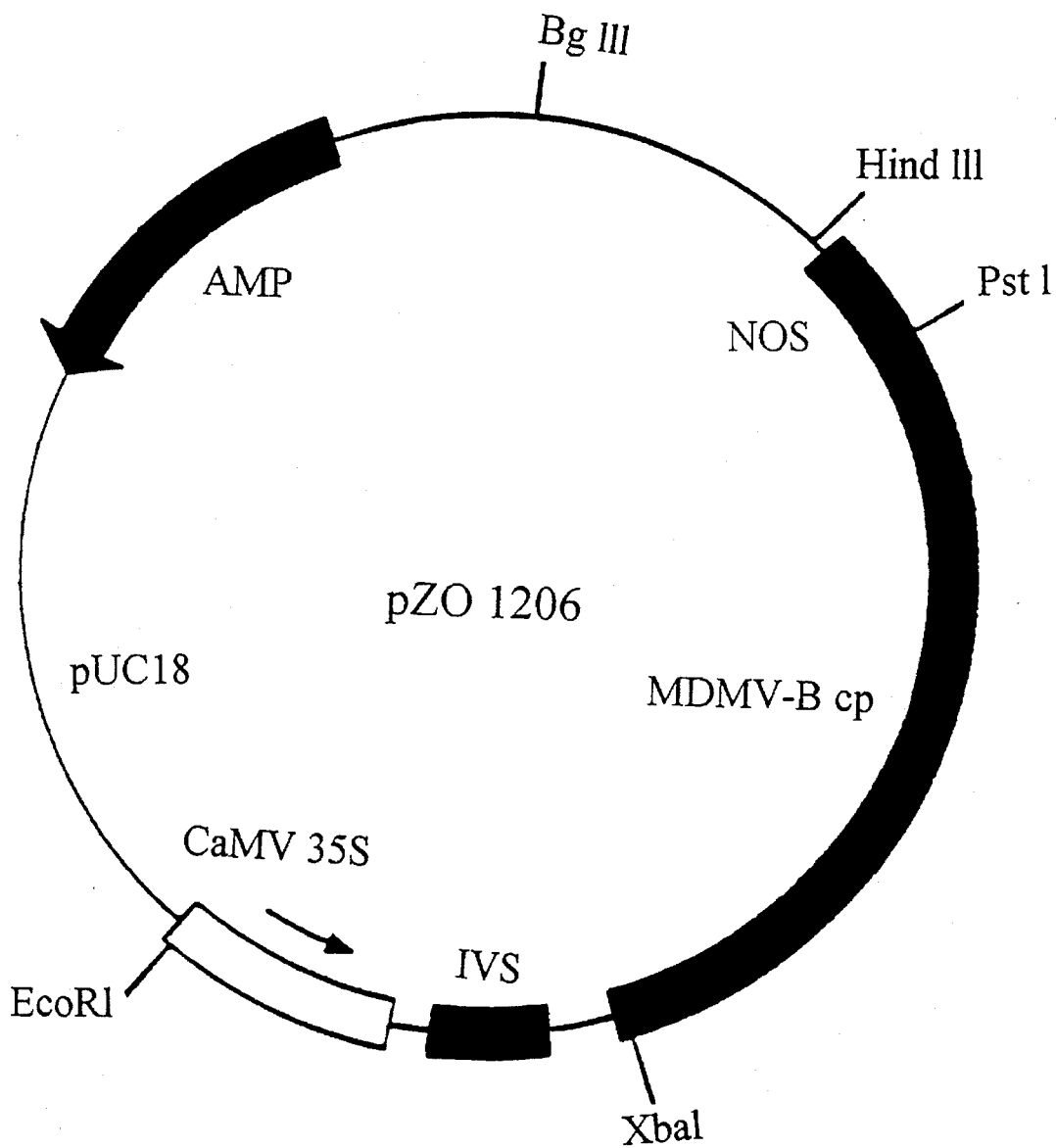
FIG. 2 is a map of pZO1206, which is a derivative of pZO1068 carrying a modified MDMV-B CP gene.

Next, the 5' end of the coat protein gene is modified to include an ATG start codon and to delete part of a polylinker present in pZO1204. To accomplish this, two oligonucleotides, LSO9MVAD (CTA GAG TCG ACC ATG TCG GG; SEQ. ID. NO. 13) and LS10MVAR (GT ACC CGACAT GGT CGA CT; SEQ. ID. NO. 14) are designed which will connect the KpnI site co the XbaI site present in the polylinker region of the transformation vector pZO1068 (detailed below; see FIG. 1), while incorporating an in-frame ATG upstream of the first Set residue. pZO1204 is restricted with Asp718 (an iso-schizomer of KpnI) and XhaI and ligated to equimolar amounts of LSO9MVAD and LS10MVAR to produce pZO1205. The coat protein genes adapted at both the 3' and 5' ends are then isolated by cutting pZO1205 with XbaI and PstI and then ligated into the vector fragment of transformation vector pZO1068, which is also are with XbaI and PstI. The resulting vector is pZO1206, as shown in FIG. 2.

Transformation vector pZO1068 is a pUC18-based monocot expression vector which also has the 35S promoter, the Adh6 intron, a polylinker containing an XbaI site at the 5' end of GUS, a PstI site at the 3' end of the GUS, and the NOS terminator.

Figure 3:
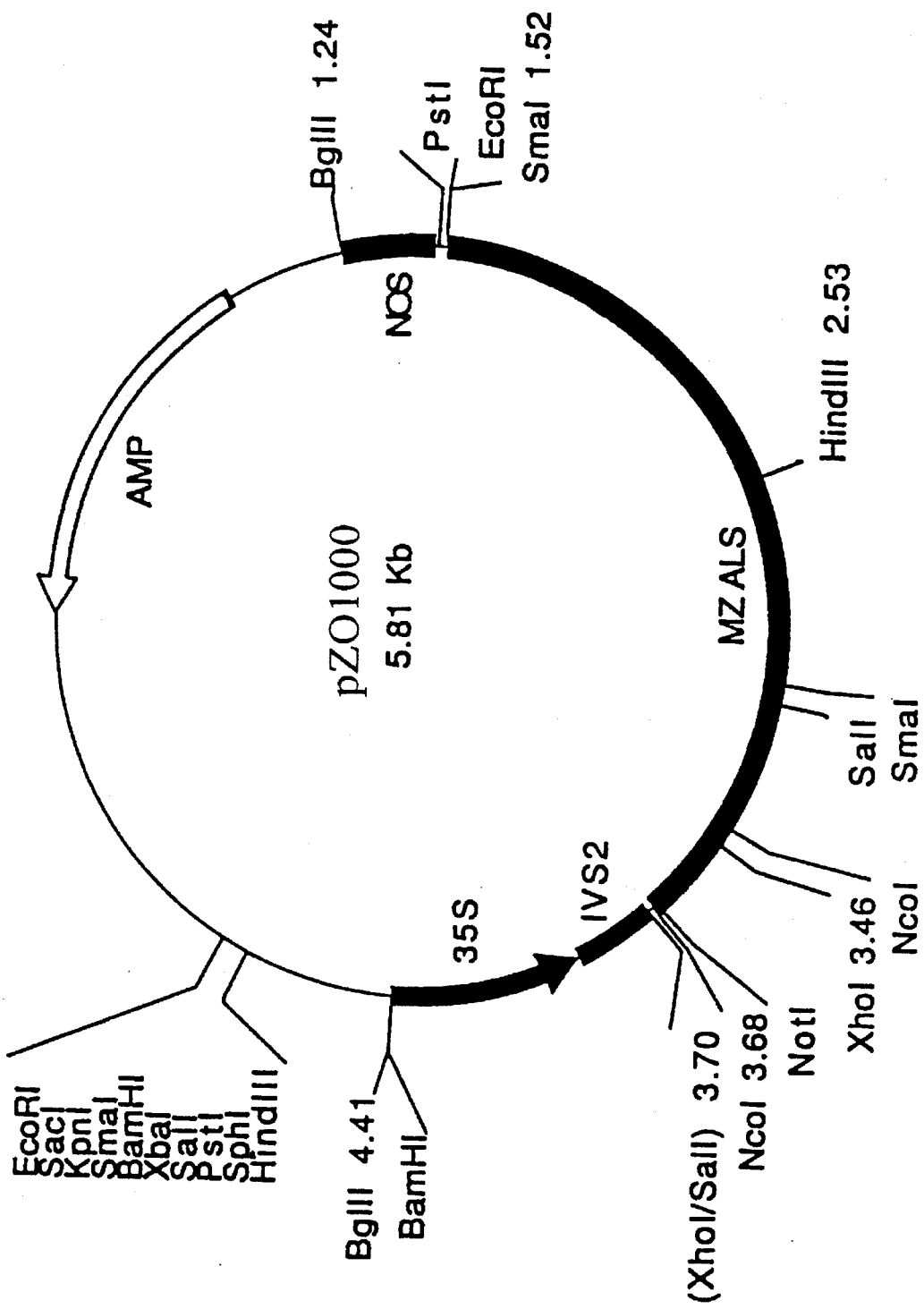
FIG. 3 is a map of pZO1000, which contains a cassette for chlorsulfuron resistance.
Figure 4:
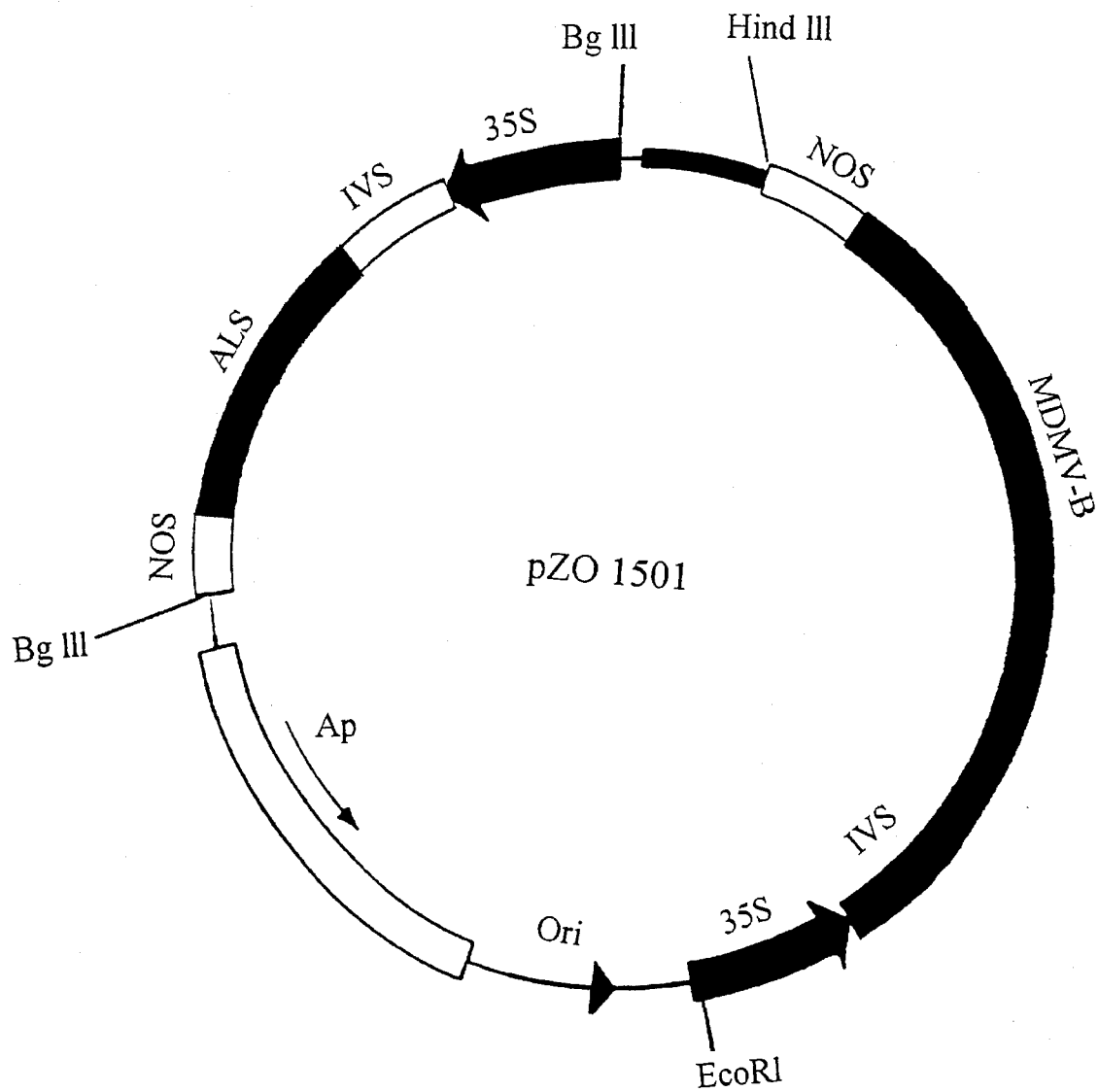
FIG. 4 is a map of pZO1501, containing the chlorsulfuron cassette and the MDMV-B CP gene.
Figure 5:
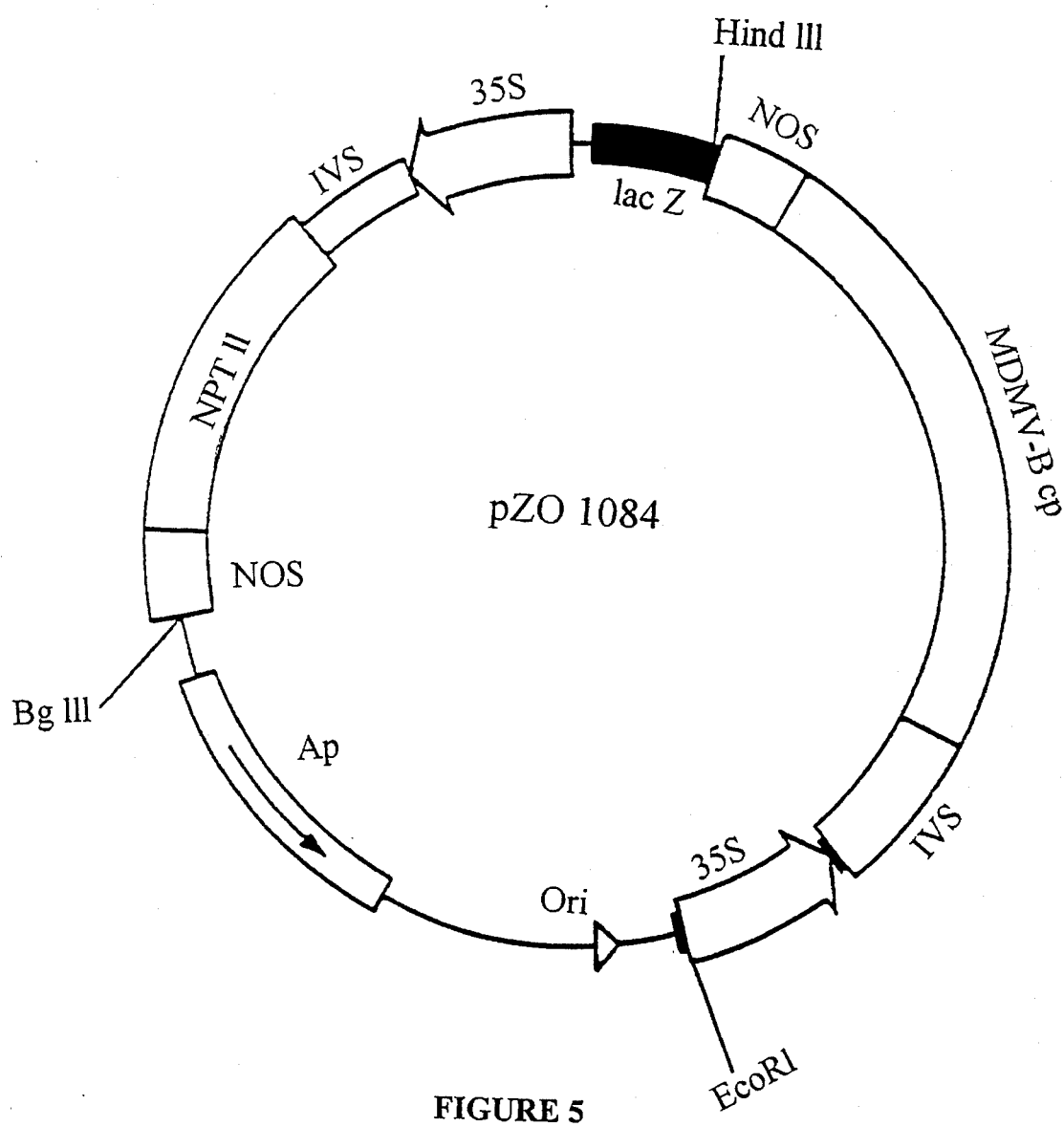
FIG. 5 is a map of pZO1084 carrying the MDMV-B CP gene cassette and a kanamycin resistance cassette.

Plamid pZO1000, a pUC19 vector containing the maize ALS (Chlorsulfuron resistance) gene (obtained from Dr. Michael Fromm and described in Fromm et al, 1990 Bio/Technology 8:833–839) which is under the control of the 35S promoter and IVS2 intron, (FIG. 3) is cut with BamHI and BglII. A 3.1 kb fragment carrying the promoter-IVS2-ALS cassette is isolated and inserted into the BlgII and PstI site of pZO1206. The resulting expression vector is designated pZO1501, shown in FIG. 4.

pZO1206 is cut with BglII and a approximately 1.9 kb kanamycin resistance cassette is inserted. This cassette contains the 35S promoter-IVS2 intron, neomycin cransferase, and the Nos terminator. The resulting plasmid, pZO1084 is shown in FIG. 5.

Figure 7:
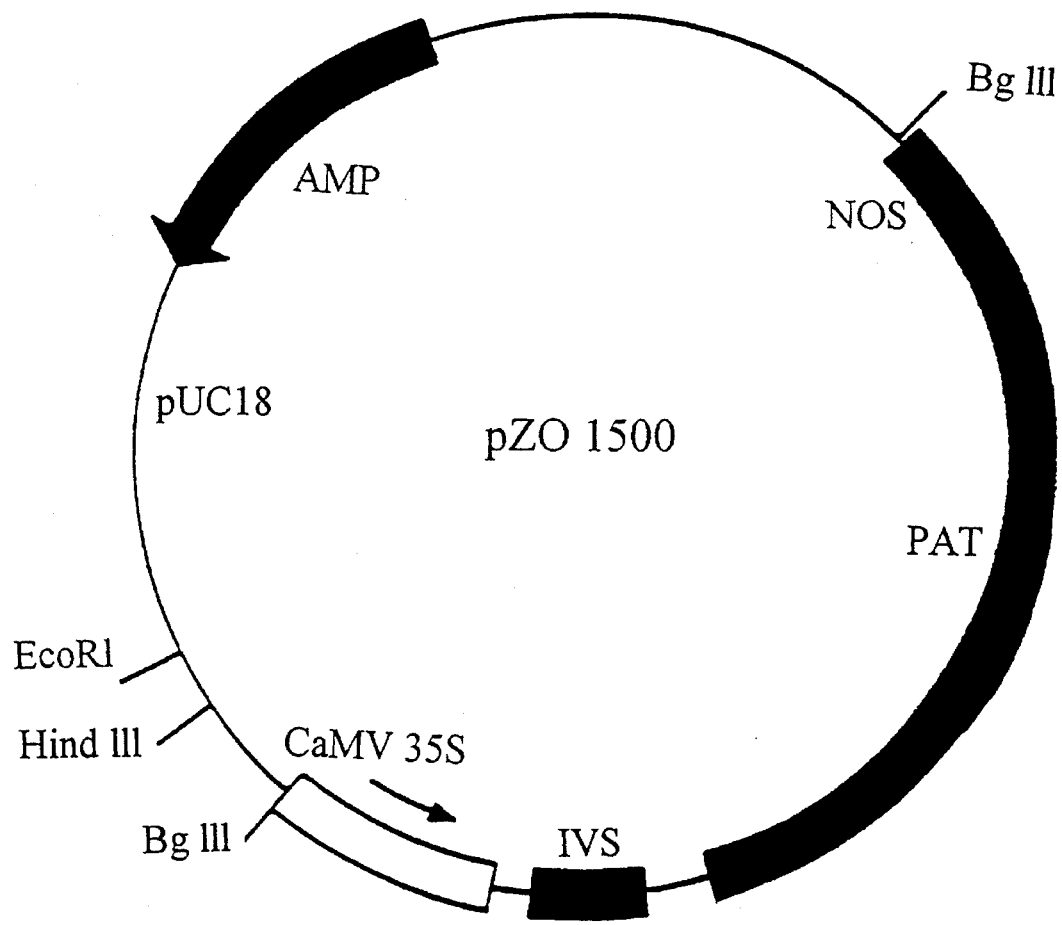
FIG. 7 is a map of pZO1500, carrying the PAT cassette.
Figure 8:
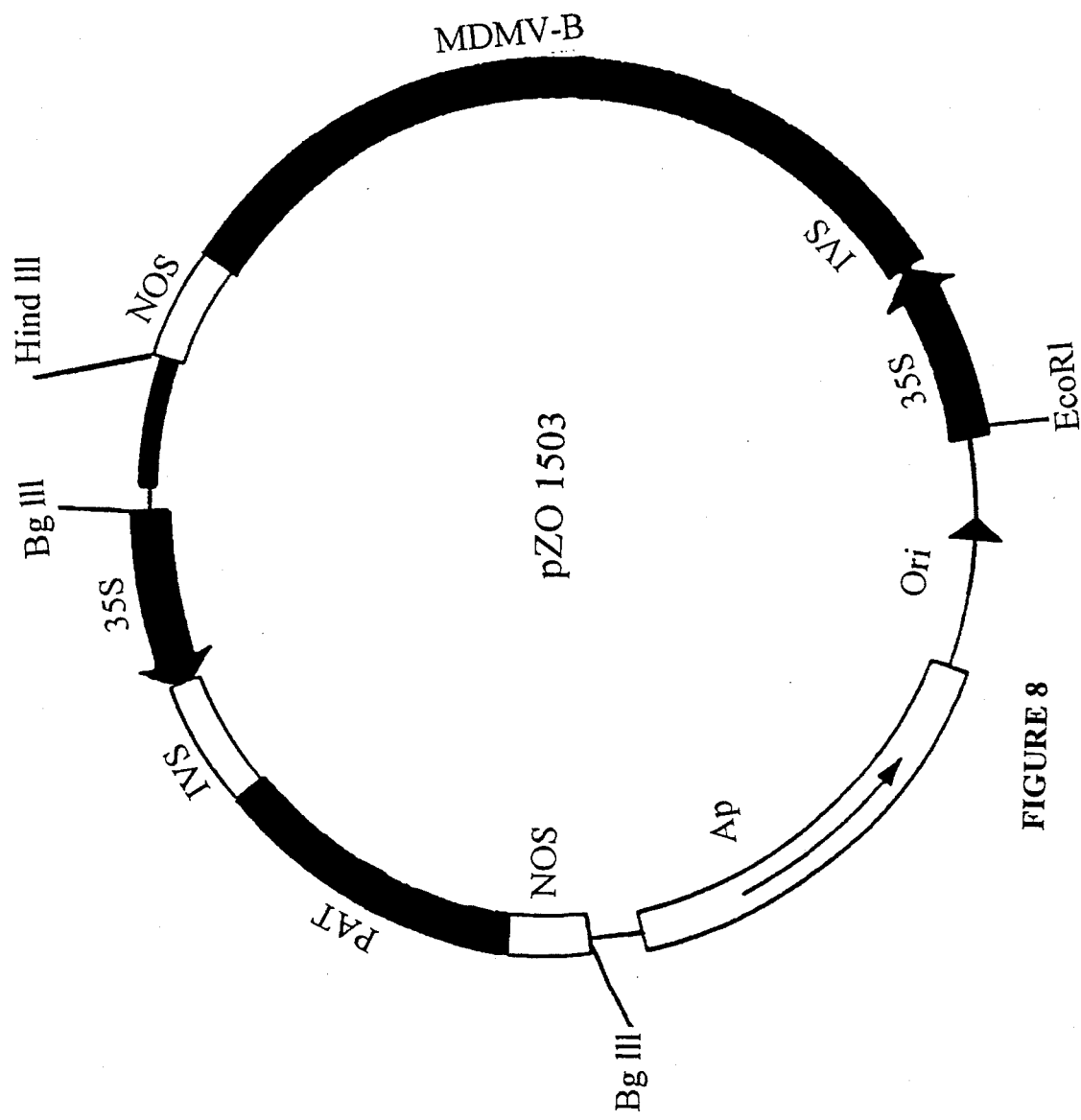
FIG. 8 is a map of pZO1503, containing the MDMV-B cassette and the PAT cassette.

The phosphinothricin acetyl cransferase (PAT) gene (Strauch, E. et al, 1988 Gene 63:65–74; Wohlleben, W. et al., 1988 Gene 70:25–37 is modified to change the initiation codon from GTG to ATG and reduce its GC content without affecting the amino acid sequence. The modified gene is obtained from Dr. P. Eckes, Hoechst AG, Frankfurt, Germany. A PAT cassette having the 35S promoter, intron 2, PAT and NOS is cloned into a pUC18 derived vector, named pZO1500 and is shown in FIG. 7. pZO1206 is digested with EcoRI and HindIII and the fragment containing the MDMV-B is isolated and then inserted into a EcoRI and HindIII digested pZO1500. The resulting vector is pZO1503, shown in FIG. 8.

MDMV-KS1 Vectors. MDMV-KS1 cDNA is also modified to include an in-frame ATG and polylinker, and this construct is inserted into plasmid pZO1068 where the GUS is deleted, as detailed in the following protocol.

Two primers for PCR mutagenesis of the MDMV-KS1 clone are synthesized. LS11MD.LP introduces a HindIII, XbaI, SalI and ATG site on the 5' end of the KS1 coat protein gene. This primer is (SEQ. ID. NO. 15): (Lower case letters indicate wild-type sequences)

| 5' CTC | AAGCTT | TCTAGA | GTCGAC | C | ATG | tca ggc aat gaa gat 3' |
|--------|--------|--------|--------|---|-----|------------------------|
|        | H3     | Xba    | Sal    |   | Met |                        |

A second primer, LS14MD.RP, generates a NsiI site (compatible with PstI) after the Stop codon of the coat protein. This primer, where lower case letters indicate wild-type sequences, is as follows: (SEQ. ID. NO.: 16)

| 3' gca ccc cgg ttt tag attACGTA CGAG 5' |
|-----------------------------------------|
| Stop- -NsiI-                            |

Figure 9:
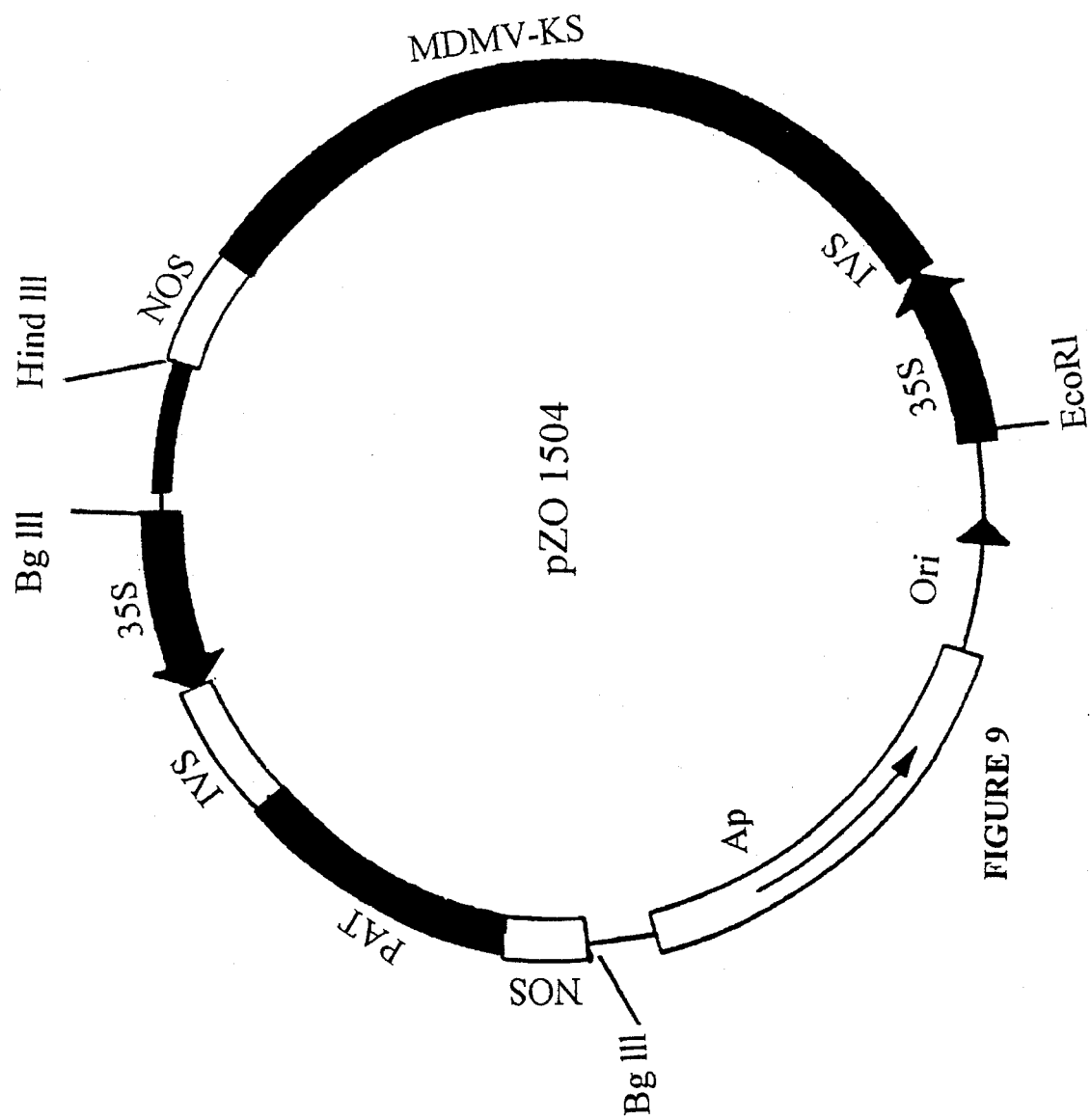
FIG. 9 is a map of pZO1504, containing the MDMV-KS1 cassette and the PAT cassette.

The MDMV-KS1 clone is cut with XbaI and EcoRI. A fragment approximately 1.5 kb long which contains the coat protein region is isolated and mutagenized by PCR amplification with primers LS11MP.LP and LS14MD.PR. The plant expression vector which will eventually carry the MDMV-KS gene, pZO1068, contains a PstI cloning site, but the MDMV-KS CP sequence also contains a PstI site. Therefore cloning of the resulting PCR-mutagenized coat protein is done in two steps. The PCR product is cut with XbaI and NsiI to purify the NsiI fragment (approximately 300 bp) containing the 3' end of the gene. This is inserted into the PstI site of pZO1068 downstream of the GUS gene. This NsiI-PstI ligation destroys both the NsiI and PstI restriction sites. The clone with the insert in the proper orientation is designated pZO1208. Next, pZO1208 is cut with XbaI and PstI and the vector fragment is purified. The mutagenized MDMV-KS product is cut with XbaI and PstI, and the 5' end coat protein fragment is ligated to the pZO1208 vector fragment, in place of the GUS gene to result in pZO1209.

pZO1209 is cut with EcoRI and HindIII and the 2.2kb fragment containing the MDMV-KS1 gene is isolated and inserted into pZO1500 which is also cut with EcoRI and HindIII. The resulting plasmid, shown in FIG. 9, is pZO1504.

MDMV-A Vectors. MDMV-A cDNA is modified substantially as described for MDMV-B cDNA to include an in-frame ATG, and polylinker, and this construct is inserted into plasmid pZO1068 where the GUS is deleted. The resulting cloning vector is designated pZOHDMV-A.

Transformation of Protoplasts. Protoplasts of various corn inbred lines and hybrids, including Black Mexican Sweet (BMS), '4191', '777', '791', and a proprietary cell line developed by Hoechst AG (Frankfurt, Germany) are prepared essentially as described by Rhodes et al, 1988a, *Bio/Technology* 6:56–60 which is hereby incorporated by reference. Plasmids carrying a MDMV gene are co-transformed with a plasmid carrying a selectable marker (SM), or a single plasmid carrying both a MDMV gene and a marker gene (as indicated in the chart below) are electroplated into protoplasts using the procedure described by Rhodes, et al, 1988b *Science* 240:204–207, which is hereby incorporated by reference. The electroplated protoplasts are placed on MS medium containing the appropriate amount of selection material and allowed to form calli. Putative transformed calli are tested for the presence of the MDMV-B, MDMV-KS1, or MDMV-A gene using PCR analysis. These tests confirm the presence of the MDMV-B, MDMV-A or MDMV-KS1 gene. Further, Northern Blot analysis show that all three clones are producing mRNA, and Western analysis confirms the production of coat protein for each clone.

Alternatively, a proprietary cell line developed by Hoechst, AG (Frankfurt, Germany) is transformed using their proprietary technique.

| Plasmids with Selectable Marker Genes | Plasmids with MDMV Genes |
|---|---|
| pZ0921 NPTII (Kanamycin resistance) | pZO1206 MDMV-B |
| pZO1000 ALS (Chlorsulfuron resistance) | pZO1209 MDMV-KS1 |
| pZO1500 PAT (Bialophos resistance) | pZOMDMV-A MDMV-A |
| Plasmids with MDMV Genes and Selectable Markers | |
| pZO1084 MDMV-B and NPTII | |
| pZO1501 MDMV-B and ALS | |
| pZO1502 MDKV-B and PAT | |
| pZO1504 MDMV-KS1 and PAT | |

Transformation of suspension cultures. A second series of transformations are performed. Various corn inbred lines, including '777' and 'Enimont S126' cell suspension cultures are transformed by particle bombardment essentially as previously described (Klein et al, 1988. *Proc, Natl. Acad. Sci.* 85:4305–4309; Gordon-Kamm et al. 1990. *Plant Cell* 2:603–618). The cells are plated on a sterile filter on appropriate selection media. The transformation mixture includes 250 82 1 PMC, 25 DNA, 50 µl spermine, 25 µl tungsten, and 225 µl water.

Figure 6:
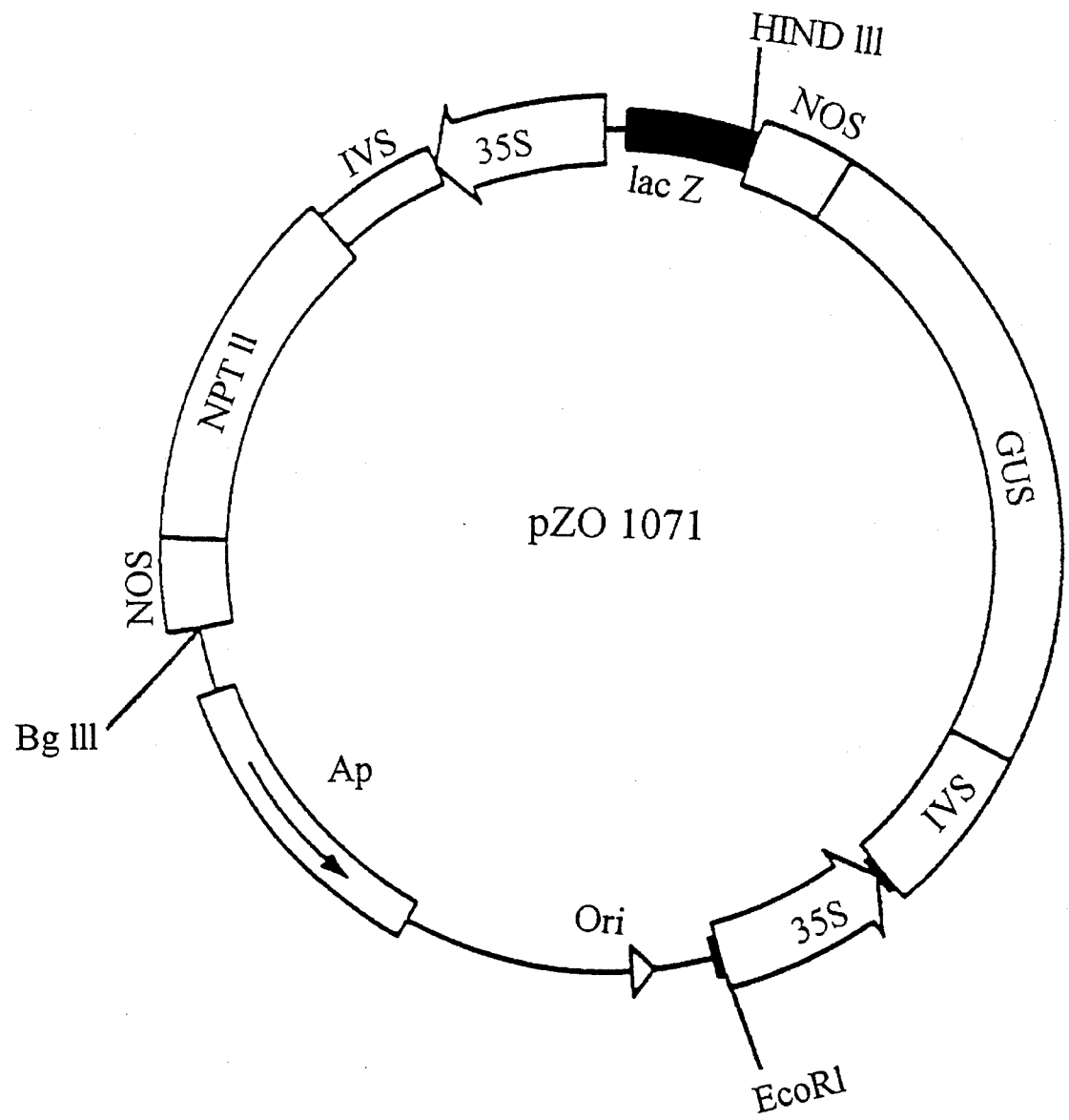
FIG. 6 is a map of pZO1071, containing the GUS gene and a kanamycin resistance cassette.

The following vectors are used to transform the cells: pZO1501, pZO1504, pZO1209+SM, pZO1084, pZOM-DMV-A+SM, and pZO1071 (contains GUS with kanamycin resistance, used for transient assays; See FIG. 6). Two plates used as controls undergo the particle bombardment procedure, but without DNA in the transformation mixture.

Two plates containing pZO1071 are screened in transient assays the day following transformation. They show 50–10,000 blue spots, respectively, indicating that the ballistic process is functioning. At this point, the cells are moved to liquid media, which is replaced after 3 days. Cells are then subjected to a selection regimen which is appropriate for each selectable marker. The selective media used is as follows: for plasmids containing NPTII, 200–300 mg/l kanamycin; for ALS plasmids, 10–60 mg/l chlorsulfuron; for PAT plasmids 0.1–2 mg/l Bialophos. After some weeks on selective media, putative transformant clumps of cells are first observed. After PCR shows that the putative transformants are positive for their respective MDMV gene, (controls are negative, as expected) the regeneration procedure begins.

5×10 mg clumps of each group of cells are transferred to 5 plates each of MS media with a varying amount of selective agent. They are subjected to a 1.5 hour cold treatment, an left in the dark for three days, then are exposed to light/darkness for 4 days, then moved to a growth chamber. After approximately 2.5 weeks, shoots and roots are beginning to form on all but the control clumps. The plantlets are transferred to magenta boxes and exposed to a maxim amount of light to avoid etiolation.

Seedlings have normal appearing root/shoot morphology, and are used in the bioassay below.

EXAMPLE 6

Bioassays

Since each corn cultivar has a differing baseline level of susceptibility to each strain of virus, it is important to determine for each plant what the proper titre of virus inoculation should be in order to test for increased tolerance. Thus, non-transformed counterpart to each corn line is innoculated with varying amounts of each virus to determine what levels of each virus results in a plant which clearly exhibits a non-lethal MDMV infection. This titre of virus is referred to as the "threshold" level. A transgenic plant is considered to have increased tolerance or resistance if it exhibits significantly fewer symptoms of MDMV infection compared to the same variety of non-transgenic plant when challenged with the "threshold" level of the same MDMV strain.

Transgenic plants (3–4 weeks old) are mechanically innoculated by wounding and applying the "threshold" level of virus (either MDMV-A, MDMV-KS1, or MDHV-B) to the leaves (usually two at this point). Non-transformed control plants of the same cultivar, and plants of the same cultivar which are transformed with an irrelevant gene are also mechanically infected with the same amount of virus.

Plants are observed until they are between 5–6 weeks old, after which time they are sacrificed. Observations include a rating of the visual assessment of the severity of the MDMV vital infection, and samples of various plant tissues are taken and analyzed for presence of the particular CP using an ELISA assay. For the control plants, regardless of the vital strain, plants exhibited severe symptoms and as expected, a high concentration of virus as quantitated by the amount of vital coat protein is present in their leaves (both innoculated and uppermost), and stem tissue. Transformed plants, on the other hand, show a significant reduction in severity of symptoms, i.e. symptoms develop at a statistically significant later time and are significantly less severe than those of the control plants. This is observed for each viral isolate. Also, the accumulation of virus as quantitated by the amount of vital coat protein is reduced in all tissues assayed, indicating that the viral infection does not spread as rapidly and that the virus does not multiply as rapidly as in control plants.

TABLE 1

MDMV-A

| GCU Ala 1 | GGU Gly | GAA Glu | AAU Asn | GUU Val 5 | GAU Asp | GCU Ala | GGG Gly | CAG Gln | AAA Lys 10 | ACU Thr | GAC Asp | GCA Ala | CAG Gln | AAG Lys 15 | GAG Glu | 48 |
|---|---|---|---|---|---|---|---|---|---|---|---|---|---|---|---|---|
| GCU Ala | GAA Glu | AAG Lys | AAA Lys 20 | GCA Ala | GCU Ala | GAG Glu | GAA Glu | AAG Lys 25 | AAA Lys | GCG Ala | AAA Lys | GAG Glu | GCC Ala 30 | GAA Glu | GCU Ala | 96 |
| AAA Lys | CAA Gln | AAA Lys 35 | GAA Glu | ACU Thr | AAG Lys | GAA Glu | AAA Lys 40 | UCA Ser | ACU Thr | GAG Glu | AAA Lys | ACU Thr 45 | GGU Gly | GAU Asp | GGU Gly | 144 |
| GGA Gly | UCC Ser 50 | AUA Ile | GGA Gly | AAA Lys | GAC Asp | AAA Lys 55 | GAU Asp | GUA Val | GAU Asp | GCU Ala | GGA Gly 60 | ACC Thr | UCA Ser | GGU Gly | UCA Ser | 192 |
| GUG Val 65 | UCA Ser | GUA Val | CCU Pro | AAG Lys | CUU Leu 70 | AAA Lys | GCU Ala | AUG Met | UCU Ser | AAG Lys 75 | AAG Lys | AUG Met | CGU Arg | UUG Leu | CCU Pro 80 | 240 |
| CAC His | GCA Ala | AAA Lys | GGA Gly | AAG Lys 85 | AAC Asn | AUU Ile | CUU Leu | CAC His | CUU Leu 90 | GAC Asp | UUC Phe | CUC Leu | UUA Leu | AAA Lys 95 | UAU Tyr | 288 |
| AAA Lys | CCA Pro | CAA Gln | CAG Gln 100 | CAA Gln | GAU Asp | UUA Leu | UCA Ser | AAC Asn 105 | ACC Thr | CGA Arg | GCA Ala | ACC Thr | AGG Arg 110 | GCU Ala | GAA Glu | 336 |
| UUU Phe | GAU Asp | AGG Arg 115 | UGG Trp | UAU Tyr | GAA Glu | GCA Ala | GUA Val 120 | CAG Gln | AAG Lys | GAA Glu | UAC Tyr | GAG Glu 125 | CUU Leu | GAU Asp | GAU Asp | 384 |
| ACA Thr | CAA Gln 130 | AUG Met | ACA Thr | GUU Val | GUC Val | AUG Met 135 | AGU Ser | GGA Gly | UUG Leu | AUG Met | GUU Val 140 | UGG Trp | UGU Cys | AUU Ile | GAA Glu | 432 |
| AAU Asn 145 | GGU Gly | UGC Cys | UCA Ser | CCG Pro | AAC Asn 150 | AUC Ile | AAC Asn | GGU Gly | CUC Leu | UGG Trp 155 | ACU Thr | AUG Met | AUG Met | GAC Asp | GGA Gly 160 | 480 |
| GAU Asp | GAA Glu | CAG Gln | ACA Thr | ACA Thr 165 | UUU Phe | CCU Pro | UUG Leu | AAA Lys | CCA Pro 170 | GUU Val | AUU Ile | AUG Met | AAU Asn | GCA Ala 175 | UCU Ser | 528 |
| CCA Pro | ACU Thr | UUU Phe | AGA Arg 180 | CAA Gln | AUU Ile | AUG Met | CAC His | CAC His 185 | UUU Phe | AGU Ser | GAU Asp | GCA Ala | GCU Ala 190 | GAA Glu | GCG Ala | 576 |
| UAU | AUU | GAA | UAU | AGA | AAU | UCA | ACA | GAA | AAA | UAU | AUG | CCA | AGA | UAU | CCA | 624 |

TABLE 1-continued

MDMV-A

| Tyr | Ile | Glu 195 | Tyr | Arg | Asn | Ser | Thr 200 | Glu | Lys | Tyr | Met | Pro 205 | Arg | Tyr | Ala | |
|---|---|---|---|---|---|---|---|---|---|---|---|---|---|---|---|---|
| CUU Leu | CAG Gln 210 | CGG Arg | AAC Asn | UUA Leu | ACC Thr | GAC Asp 215 | UUU Phe | AGC Ser | CUU Leu | GCA Ala | CGU Arg 220 | UAU Tyr | GCA Ala | UUU Phe | GAU Asp | 672 |
| UUC Phe 225 | UAU Tyr | GAG Glu | AUA Ile | UCA Ser | UCU Ser 230 | CGA Arg | ACU Thr | CCA Pro | GUG Val | CGC Arg 235 | GCA Ala | AAG Lys | GAA Glu | GCC Ala | CAC His 240 | 720 |
| AUG Met | CAG Gln | AUG Met | AAA Lys | GCA Ala 245 | GCA Ala | CCA Pro | GGU Gly 250 | UCA Ser | AAC Asn | ACA Thr | CGG Arg | AUG Met 255 | UUC Phe | 768 | | |
| GGU Gly | CUU Leu | GAU Asp | GCG Gly 260 | AAU Asn | CUC Val | GGA Gly | GAA Glu | GCC Ala 265 | CAC His | GAA Glu | AAU Asn | ACA Thr | GAA Glu 270 | CGC Arg | CAC His | 816 |
| ACA Thr | GCU Ala | GAU Asp | GUC Val | AGU Ser | CCG Pro | AAU Asn 280 | AUG Met | CAC His | UCC Ser | CUU Leu | CUG Leu 285 | GGG Gly | CUC Val | CAG Gln | 864 | |
| CAA Gln | GGC Gly 275 | UGAUACGGGG | | UUUAACUUUU | | ACGCAGUAAU | | | | UUAGUAAUAU | | | | 913 | | |
| AUAAUUAAGC | CAC His 290 | UAUUGUGGUG | | AGGUUUUACC | | UCGUUAGUUU | | UCGUUAGUUU | | UAUUUAUAUA | | | | 973 | | |
| UACCUGCUAU | | GUCUGCAACU | | GAGUGAGGUU | | AUACCUCGAC | | | | ACUUAUAGUA | | GGCACAUUUA | | 1033 | | |
| CUAGCUUCGA | | AUCACGAGAC | | GGACCAUCCA | | UUGAGUGGUU | | | | CUACCACUGC | | AGGAUGCAGC | | 1093 | | |
| GAGUUUCGUG | | GUGAGAGACA | | | | | | | | | | | | 1113 | | |

TABLE 2

| MDMV-B | | | | | | | | | | | | | | | | |
|---|---|---|---|---|---|---|---|---|---|---|---|---|---|---|---|---|
| UCC<br>Ser<br>1 | GGA<br>Gly | ACU<br>Thr | GUU<br>Val | GAU<br>Asp<br>5 | GCG<br>Ala | GGU<br>Gly | GCA<br>Ala | CAA<br>Gln | GGC<br>Gly<br>10 | GGC<br>Gly | ACU<br>Ser | GGA<br>Gly | ACC<br>Ser | CAA<br>Gln<br>15 | GGG<br>Gly | 48 |
| ACA<br>Thr | ACA<br>Thr | CCA<br>Pro | CCA<br>Pro<br>20 | GCA<br>Ala | ACA<br>Thr | GGU<br>Gly | AGU<br>Ser | GGA<br>Gly<br>25 | GCA<br>Ala | AAA<br>Lys | CCA<br>Pro | GCC<br>Ala | ACC<br>Thr<br>30 | UCA<br>Ser | GGG<br>Gly | 96 |
| GCA<br>Ala | GGA<br>Gly | UCU<br>Ser<br>35 | GGU<br>Gly | AGU<br>Ser | GGC<br>Gly | ACA<br>Thr | GGA<br>Gly<br>40 | GCU<br>Ala | GGA<br>Gly | ACU<br>Thr | GGU<br>Gly | GUA<br>Val<br>45 | ACU<br>Thr | GGA<br>Gly | GGU<br>Gly | 144 |
| CAA<br>Gln | GCA<br>Ala<br>50 | AGG<br>Arg | ACU<br>Thr | GGC<br>Gly | AGU<br>Ser | GGC<br>Gly<br>55 | ACU<br>Thr | GGG<br>Gly | ACG<br>Thr | GGA<br>Gly | UCU<br>Ser<br>60 | GGA<br>Gly | GCA<br>Ala | ACC<br>Thr | GGA<br>Gly | 192 |
| GGC<br>Gly<br>65 | CAA<br>Gln | UCA<br>Ser | GGA<br>Gly | UCU<br>Ser | GGA<br>Gly<br>70 | AGU<br>Ser | GGC<br>Gly | ACU<br>Thr | GAA<br>Glu | CAG<br>Gln<br>75 | GUU<br>Val | AAC<br>Asn | ACG<br>Thr | GGU<br>Gly | UCA<br>Ser<br>80 | 240 |
| GCA<br>Ala | GGA<br>Gly | ACU<br>Thr | AAU<br>Asn | GCA<br>Ala<br>85 | ACU<br>Thr | GGA<br>Gly | GGC<br>Gly | CAA<br>Gln | AGA<br>Arg<br>90 | GAU<br>Asp | AGG<br>Arg | GAU<br>Asp | GUG<br>Val | GAU<br>Asp<br>95 | GCA<br>Ala | 288 |
| GGC<br>Gly | UCA<br>Ser | ACA<br>Thr | GGA<br>Gly<br>100 | AAA<br>Lys | AUU<br>Ile | UCU<br>Ser | GUA<br>Val | CCA<br>Pro<br>105 | AAG<br>Lys | CUC<br>Leu | AAG<br>Lys | GCC<br>Ala | AUG<br>Met<br>110 | UCA<br>Ser | AAG<br>Lys | 336 |
| AAA<br>Lys | AUG<br>Met | CGC<br>Arg<br>115 | UUA<br>Leu | CCU<br>Pro | AAA<br>Lys | GCA<br>Ala | AAA<br>Lys<br>120 | GGA<br>Gly | AAA<br>Lys | GAU<br>Asp | GUG<br>Val | CUA<br>Leu<br>125 | CAU<br>His | UUG<br>Leu | GAU<br>Asp | 384 |
| UUU<br>Phe | CUA<br>Leu<br>130 | UUG<br>Leu | ACA<br>Thr | UAU<br>Tyr | AAA<br>Lys | CCA<br>Pro<br>135 | CAA<br>Gln | CAA<br>Gln | CAA<br>Gln | GAC<br>Asp | AUA<br>Ile<br>140 | UCA<br>Ser | AAC<br>Asn | ACU<br>Thr | AGA<br>Arg | 432 |
| GCA<br>Ala<br>145 | ACC<br>Thr | AAG<br>Lys | GAA<br>Glu | GAG<br>Glu | UUU<br>Phe<br>150 | GAU<br>Asp | AGA<br>Arg | UGG<br>Trp | UAU<br>Tyr | GAU<br>Asp<br>155 | GCC<br>Ala | AUA<br>Ile | AAG<br>Lys | AAC<br>Lys | GAA<br>Glu<br>160 | 480 |
| UAC<br>Tyr | GAA<br>Glu | AUU<br>Ile | GAU<br>Asp | GAC<br>Asp<br>165 | ACA<br>Thr | CAA<br>Gln | AUG<br>Met | ACA<br>Thr | GUU<br>Val<br>170 | GUC<br>Val | AUG<br>Met | AGU<br>Ser | GGC<br>Gly | CUU<br>Leu<br>175 | AUG<br>Met | 528 |
| GUA<br>Val | UGG<br>Trp | UGC<br>Cys | AUC<br>Ile<br>180 | GAA<br>Glu | AAU<br>Asn | GGU<br>Gly | UGC<br>Cys | UCA<br>Ser<br>185 | CCA<br>Pro | AAC<br>Asn | AUA<br>Ile | AAC<br>Asn | GGA<br>Gly<br>190 | AAU<br>Asn | UGG<br>Trp | 576 |
| ACA | AUG | AUG | GAU | AAA | GAU | GAA | CAA | AGG | GUC | UUC | CCA | CUC | AAA | CCG | CUC | 624 |

TABLE 2-continued

MDMV-B

| Thr | Met | Asp | Lys | Asp | Glu | Gln 200 | Arg | Val | Phe | Pro | Leu 205 | Lys | Pro | Val | |
|---|---|---|---|---|---|---|---|---|---|---|---|---|---|---|---|
| AUU Ile | GAG Glu 210 | GCA Ala | UCU Ser | CCA Pro | ACU Thr 215 | UUC Phe | CGA Arg | CAA Gln | AUU Ile | AUG Met 220 | CAU His | CAU His | UUC Phe | AGU Ser | 672 |
| GAU Asp 225 | GCU Ala | GAA Glu | GCG Ala | UAC Tyr 230 | AUA Ile | GAG Glu | UAC Tyr | AGA Arg | AAC Asn 235 | UCU Ser | ACU Thr | GAG Glu | AGC Ser | UAU Tyr 240 | 720 |
| AUG Met | AGA Arg | CCA Pro | GGA Gly 245 | CUU Leu | CAG Gln | CGC Arg | AAU Asn | UCA Ser | GAC Asp | CGC Arg | UAU Tyr | CCU Pro 270 | UUA Leu 255 | GCA Ala | 768 |
| CGG Arg | UAU Tyr | UUU Phe 260 | GAU Asp | UUC Phe | UAU Tyr | AUG Met 265 | ACU Thr | UCA Ser | ACU Thr | UAU Tyr | ACA Thr | CGU Arg | GCU Ala | AGA Arg | 816 |
| GCU Ala | AAA Lys | GCC Ala | CAC His | AUG Met | CAG Gln | GAA Glu 280 | AUG Met | GCC Ala | UCA Ser | GCA Ala | GUU Val 285 | CGU Arg | GGU Gly | UCC Ser | 864 |
| AAC Asn | ACA Thr 290 | CUG Leu | UUC Phe | CCU Gly | UUG Leu 295 | GAC Asp | GGA Gly | AAU Asn | GUC Val | GGC Gly 300 | GAG Glu | ACU Thr | CAG Gln | GAG Glu | 912 |
| AAU Asn 305 | ACA Thr | AGA Arg | CAC His | ACA Thr 310 | GCU Ala | GGC Gly | GAU Asp | GUU Val | AGU Ser 315 | CGC Arg | AAC Asn | AUG Met | CAC His | UCU Ser 320 | 960 |
| CUG Leu | UUG Leu | GUG Val | CAG Gln 325 | CAA Gln | CAC His | | | | | | | | UUGCAGUACC | | 1014 |
| AAUAAUAUAU | | ACUAAUAUAU | | AGUAUUUAG | | | | UGAGUUUUA | | CCUCGUCUUU | | | ACUCUUUAU | | 1074 |
| UACCUAUGUA | | UUUAAAGCGU | | GAACCAGUCU | | | | GCAACAUACA | | GGGUUGGACC | | | CAGUGUGUUC | | 1134 |
| UGGUCUAGCG | | UCUACUAGCG | | UCCAGCCAUG | | | | AGAUGGACUG | | CACUGGGUGU | | | GGUUUGCCA | | 1194 |
| CUUGUGUUGC | | GAGUCUCUGG | | UAAGAGA | | | | | | | | | | | 1221 |

TABLE 3

MDMV-KS1

| | | | | | | | | | | | | | | | | |
|---|---|---|---|---|---|---|---|---|---|---|---|---|---|---|---|---|
| UCA Ser 1 | GGC Gly | AAU Asn | GAA Glu | GAU Asp 5 | GCU Ala | GGA Gly | AGA Arg | CAG Gln | AAG Lys 10 | AGU Ser | GCA Ala | CCA Pro | GCU Ala 15 | GAA Glu | | 48 |
| AAC Asn | AAA Lys | CCA Pro | GCU Ala 20 | AGU Ser | GGU Gly | AGU Ser | CCA Pro | AAA Lys 25 | GCA Ala | CAA Gln | ACA Thr 30 | CAA Gln | ACG Thr | GCG Ala | ACA Thr | 96 |
| UCA Ser | CCA Pro | AAC Asn 35 | GAC Asp | AAC Asn | CCA Pro | UCU Ser | GAU Asp 40 | UCU Ser | ACU Thr | AAU Asn | ACU Thr 45 | CAA Gln | AAU Asn | GGA Gly | ACA Thr | 144 |
| UCA Ser | CAA Gln 50 | GCC Ala | AAA Lys | AAG Lys | GAU Asp | AGU Ser 55 | GGA Gly | AGU Ser | UCA Ser | ACA Thr 60 | AAU Asn | GCC Ala | GAC Asp | GGA Gly | ACG Thr | 192 |
| GCA Ala 65 | ACG Thr | AAA Lys | AAA Lys | GAU Asp 70 | AAG Lys | CUC Val | GUU Val | UCA Ser 75 | ACC Thr | GUA Leu | ACU Thr | CCC Pro | ACG Thr 80 | UUU Phe | GUG Val | 240 |
| AUU Ile | CCG Pro | AAA Lys | AAG Lys | AAG Lys 85 | CUC Leu | GAU Asp | AUG Met | CAU His 90 | UUA Leu | CCC Pro | CCU Arg | AUC Ile | CAG Gln | GUG Val | CCA Pro | 288 |
| AGC Ser | AAC Asn | AAA Lys | AGA Arg 115 | GCC Ala | UCG Ser | CCU Arg | ACA Thr | AUC Ile | CAC His | ACA Thr 125 | CCC Pro | CAA Gln | | | | 336 |
| GAC Asp | CAG Gln | AGA Arg 115 | GCU Ala 120 | AAG Lys | UUA Leu | ACA Thr | ACA Thr | GUU Val 140 | GAU Asp | AUA Ile | GAC Asp | GGA Gly | CAA Gln | | | 384 |
| UUC Phe | UGG Trp 130 | UAC Tyr | UCG Ser | AAG Lys 135 | UAC Tyr | CCC Pro | UGG Trp 155 | UCU Cys | AUG Met | GAG Glu | UUC Phe | CAA Gln | | | | 432 |
| AUG Met 145 | AGG Arg | AUC Ile | AUG Met | GGA Gly | AAC Asn 150 | UUA Leu | AUG Met | UGG Trp | AUA Ile | GUU Val 140 | GAU Asp | GAU Asp | GGA Gly | CCA Pro | CAA Gln | 480 |
| ACA Thr | UCU Ser | CCU Pro | GAU Asp | AAU Asn | AAU Asn | AUA Ile 165 | UGG Trp | ACC Thr 170 | GAU Asp | CAC His | AUC Ile | UCU Cys | GUG Val | AAU Asn | AAC Asn 175 | 528 |
| CAA Gln | UCU Ser | GAA Glu | UUU Phe 180 | CCA Pro | CUA Leu | CAU His? | AUA Ile 185 | UAC Tyr | CCA Pro | UCA Ser | GAA Glu | GGA Gly | GCA Ala | AAA Lys 190 | CCA Pro | 576 |
| UUA | CGA | UGC | UUU | AUG | AGU | CAU | GAC | GCC | AGU | UAC | AUU | | | | | 624 |

TABLE 3-continued

MDMV-KS1

| | | Leu | Arg | Gln 195 | Cys | Met | Met | His | Phe 200 | Ser | Ala | Asp | Ala | Glu 205 | Ala | Tyr | Ile | |
|---|---|---|---|---|---|---|---|---|---|---|---|---|---|---|---|---|---|---|
| | | GAA Glu | AUG Met 210 | AGA Arg | AAU Asn | UUG Leu | GAU Asp | GAG Glu 215 | CCG Pro | UAC Tyr | CCA Pro | AUG Met | AGA Arg 220 | UAC Tyr | GGU Gly | CUC Leu | CUU Leu | 672 |
| | | AGG Arg 225 | CUA Leu | AAU Asn | GAC Asp | AAG Lys 230 | AGC Ser | CUC Leu | GCU Ala | UAC Tyr 235 | GCA Ala | GAU Asp | UUU Phe | GAU Asp | UUC Phe | UAU Tyr 240 | | 720 |
| | | GAG Glu | AAU Asn | UCG Ser | CCC Arg 245 | GCA Ala | ACG Thr | AUU Ile | CCA Pro | AGA Arg | GCG Ala 250 | GAG Glu | CAU His | GCA Ala 255 | CAA Gln | | | 768 |
| | | AUG Met | AAG Lys | GCA Ala | GCA Ala | GUU Val | GGA Gly | UCU Ser 265 | AAU Asn | ACA Thr | AAC Asn | CAC His | UUU Phe 270 | GGA Gly | CUC Leu | | | 816 |
| | | GAC Asp | GGG Gly | AAU Asn 275 | AGC Ser | CGG Arg | GAG Glu | UCU Ser 280 | AGC Ser | AAU Asn | ACA Thr | AUG Met | CAC His | CGG Arg 285 | ACA Thr | GCU Ala | | 864 |
| | | GCA Ala | GAU Asp 290 | CUC Val | UCA Ser | CGG Arg | AAU Asn | CAU His | GUC Val 295 | UCG Ser | UAC Tyr | CCU Arg | GCC Ala | AUC Ile | AAA Lys | | UAAGGAGGAG | 919 |
| | | GAACAACCGU | | CUAUCUGACG | | UUAAAGGAUG | | ACUGGCCAAG | UCUGAAAAUU | GGCGUGAUAC | | | | | | | | 979 |
| | | CAGUUCCGAA | | UAGUCCAUAC | | AGAAUUAGAG | | CUGAACAGAG | AGCACUAUAA | AGGUUUAGUA | | | | | | | | 1039 |
| | | GGGAUCGAGA | | GAUGACACGU | | AGGACCUCAA | | UGACCAUGCU | UAGCGCUAGC | AUUGUGUGGA | | | | | | | | 1099 |
| | | GCUCUAACAC | | UCACGUCUUA | | UCUUCCAGGC | | UGUGGUAAUC | UCGUACCCCG | AAGUACCUAU | | | | | | | | 1159 |
| | | GGGCCCUCAG | | CACCAGACAG | | UACUGGGACU | | AUGUAUCCUU | UCUUGGCAAU | CAGUAGUAUU | | | | | | | | 1219 |
| | | AUAAAUCGUU | | CUCCAACGGC | | ACGAGUGGUG | | UUUUACACCU | GGGUGGAAUC | CUAAUGCUCU | | | | | | | | 1279 |
| | | UAUACAGUUA | | UGGAUAACGG | | CCCGUGUUGU | | UAGUUUUUAC | UAGUUGCAUC | AGACCAUCUG | | | | | | | | 1339 |
| | | AGCCUCAGAG | | UGAGCUUCUC | | ACCACGCAGU | | CUCUUAUGGC | GAGAUA | | | | | | | | | 1385 |

What is claimed is:

1. A transgenic corn plant whose genome comprises a DNA sequence which encodes a coat protein of a potyvirus selected from the group consisting of Maize Dwarf Mosaic Virus Strain A (MDMV-A), Maize Dwarf Mosaic Virus Strain B (MDMV-B) and Maize Dwarf Mosaic Virus Strain KS-1 (MDMV-KS-1) wherein said corn plant is resistant or tolerant to a strain of Maize Dwarf Mosaic Virus.

2. A transgenic corn plant according to claim 1 wherein the DNA sequence encodes a coat protein of Maize Dwarf Mosaic Virus Strain A (MDMV-A).

3. A transgenic corn plant according to claim 1 wherein the DNA sequence encodes a coat protein of Maize Dwarf Mosaic Virus Strain B (MDMV-B).

4. A transgenic corn plant according to claim 1 wherein the DNA sequence encodes a coat protein of Maize Dwarf Mosaic Virus Strain KS-1 (MDMV-KS-1).

5. A transgenic corn plant according to claim 1 further comprising resistance to a carnivorous, maize chlorotic mottle virus.

6. A transgenic corn plant according to claim 1 wherein said corn plant is sweet corn.

7. A transgenic corn plant according to claim 1 wherein said corn plant is field corn.

8. The seed of the transgenic corn plant according to claim 1.

9. A method of conferring resistance or tolerance in a corn plant to viral infection by a strain of Maize Dwarf Mosaic Virus comprising inserting into the plant's genome one or more copies of a gene encoding a coat protein of a potyvirus selected from the group consisting of Maize Dwarf Mosaic Virus Strain A (MDMV-A), Maize Dwarf Mosaic Virus Strain B (MDMV-B) and Maize Dwarf Mosaic Virus Strain KS-1 (MDMV-KS-1).

* * * * *

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
      ( A ) LENGTH: 1113 base pairs
      ( B ) TYPE: nucleic acid
      ( C ) STRANDEDNESS: single
      ( D ) TOPOLOGY: linear ( i x ) FEATURE:
      ( A ) NAME/KEY: CDS
      ( B ) LOCATION: 1..876

( x i ) SEQUENCE DESCRIPTION: SEQ ID NO:1:

```
GCU  GGU  GAA  AAU  GUU  GAU  GCU  GGG  CAG  AAA  ACU  GAC  GCA  CAG  AAG  GAG        48
Ala  Gly  Glu  Asn  Val  Asp  Ala  Gly  Gln  Lys  Thr  Asp  Ala  Gln  Lys  Glu
 1                    5                        10                       15

GCU  GAA  AAG  AAA  GCA  GCU  GAG  GAA  AAG  AAA  GCG  AAA  GAG  GCC  GAA  GCU        96
Ala  Glu  Lys  Lys  Ala  Ala  Glu  Glu  Lys  Lys  Ala  Lys  Glu  Ala  Glu  Ala
             20                       25                       30

AAA  CAA  AAA  GAA  ACU  AAG  GAA  AAA  UCA  ACU  GAG  AAA  ACU  GGU  GAU  GGU       144
Lys  Gln  Lys  Glu  Thr  Lys  Glu  Lys  Ser  Thr  Glu  Lys  Thr  Gly  Asp  Gly
        35                       40                       45

GGA  UCC  AUA  GGA  AAA  GAC  AAA  GAU  GUA  GAU  GCU  GGA  ACC  UCA  GGU  UCA       192
Gly  Ser  Ile  Gly  Lys  Asp  Lys  Asp  Val  Asp  Ala  Gly  Thr  Ser  Gly  Ser
    50                       55                       60

GUG  UCA  GUA  CCU  AAG  CUU  AAA  GCU  AUG  UCU  AAG  AAG  AUG  CGU  UUG  CCU       240
Val  Ser  Val  Pro  Lys  Leu  Lys  Ala  Met  Ser  Lys  Lys  Met  Arg  Leu  Pro
65                        70                       75                       80

CAG  GCA  AAA  GGA  AAG  AAC  AUU  CUU  CAC  CUU  GAC  UUC  CUC  UUA  AAA  UAU       288
Gln  Ala  Lys  Gly  Lys  Asn  Ile  Leu  His  Leu  Asp  Phe  Leu  Leu  Lys  Tyr
                 85                       90                       95

AAA  CCA  CAA  CAG  CAA  GAU  UUA  UCA  AAC  ACC  CGA  GCA  ACC  AGG  GCU  GAA       336
Lys  Pro  Gln  Gln  Gln  Asp  Leu  Ser  Asn  Thr  Arg  Ala  Thr  Arg  Ala  Glu
            100                      105                      110

UUU  GAU  AGG  UGG  UAU  GAA  GCA  GUA  CAG  AAG  GAA  UAC  GAG  CUU  GAU  GAU       384
Phe  Asp  Arg  Trp  Tyr  Glu  Ala  Val  Gln  Lys  Glu  Tyr  Glu  Leu  Asp  Asp
        115                      120                      125

ACA  CAA  AUG  ACA  GUU  GUC  AUG  AGU  GGA  UUG  AUG  GUU  UGG  UGU  AUU  GAA       432
Thr  Gln  Met  Thr  Val  Val  Met  Ser  Gly  Leu  Met  Val  Trp  Cys  Ile  Glu
        130                      135                      140

AAU  GGU  UGC  UCA  CCG  AAC  AUC  AAC  GGU  GUC  UGG  ACU  AUG  AUG  GAC  GGA       480
Asn  Gly  Cys  Ser  Pro  Asn  Ile  Asn  Gly  Val  Trp  Thr  Met  Met  Asp  Gly
145                      150                      155                      160

GAU  GAA  CAG  AGA  ACA  UUU  CCU  UUG  AAA  CCA  GUU  AUU  GAA  AAU  GCA  UCU       528
Asp  Glu  Gln  Arg  Thr  Phe  Pro  Leu  Lys  Pro  Val  Ile  Glu  Asn  Ala  Ser
                165                      170                      175

CCA  ACU  UUC  AGA  CAA  AUU  AUG  CAC  CAC  UUU  AGU  GAU  GCA  GCU  GAA  GCG       576
Pro  Thr  Phe  Arg  Gln  Ile  Met  His  His  Phe  Ser  Asp  Ala  Ala  Glu  Ala
           180                      185                      190

UAU  AUU  GAA  UAU  AGA  AAU  UCA  ACA  GAA  AAA  UAU  AUG  CCA  AGA  UAU  GCA       624
Tyr  Ile  Glu  Tyr  Arg  Asn  Ser  Thr  Glu  Lys  Tyr  Met  Pro  Arg  Tyr  Ala
        195                      200                      205

CUU  CAG  CGG  AAC  UUA  ACC  GAC  UUU  AGC  CUU  GCA  CGU  UAU  GCA  UUU  GAU       672
Leu  Gln  Arg  Asn  Leu  Thr  Asp  Phe  Ser  Leu  Ala  Arg  Tyr  Ala  Phe  Asp
        210                      215                      220

UUC  UAU  GAG  AUA  UCA  UCU  CGA  ACU  CCA  GUG  CGC  GCA  AAG  GAA  GCC  CAC       720
Phe  Tyr  Glu  Ile  Ser  Ser  Arg  Thr  Pro  Val  Arg  Ala  Lys  Glu  Ala  His
```

```
                225                       230                       235                       240
AUG  CAG  AUG  AAA  GCA  GCA  GCA  GUC  CGU  GGU  UCA  AAC  ACA  CGG  AUG  UUC           768
Met  Gln  Met  Lys  Ala  Ala  Ala  Val  Arg  Gly  Ser  Asn  Thr  Arg  Met  Phe
                    245                      250                      255

GGU  CUU  GAU  GGG  AAU  GUC  GGA  GAA  GCC  CAC  GAA  AAU  ACA  GAA  CGC  CAC           816
Gly  Leu  Asp  Gly  Asn  Val  Gly  Glu  Ala  His  Glu  Asn  Thr  Glu  Arg  His
               260                      265                      270

ACA  GCU  GGC  GAU  GUC  AGU  CCG  AAU  AUG  CAC  UCC  CUU  CUG  GGG  GUC  CAG           864
Thr  Ala  Gly  Asp  Val  Ser  Pro  Asn  Met  His  Ser  Leu  Leu  Gly  Val  Gln
          275                      280                      285

CAA  GGC  CAC  UGAUACGGGG  UUUAACUUUU  ACGCAGUAAU  UUAGUAAUAU                              913
Gln  Gly  His
290

AUAAUUAAGC  UAUUGUGGUG  AGGUUUUACC  UCGUUAGUUU  UAUUUAUAUA  UUAUGCUACG                    973

UACCUGCUAU  GUCUGCAAGU  GAGUGAGGUU  AUACCUCGAC  ACUUAUAGUA  GGCACUAUUA                   1033

CUAGCUUCGA  AUCACGAGAC  GGACGAUCCA  UUGAGUGGUU  CUACCACUGC  AGGAUGCAGC                   1093

GAGUUUCGUG  GUGAGAGACA                                                                  1113
```

( 2 ) INFORMATION FOR SEQ ID NO:2:

( i ) SEQUENCE CHARACTERISTICS:
        ( A ) LENGTH: 291 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Ala  Gly  Glu  Asn  Val  Asp  Ala  Gly  Gln  Lys  Thr  Asp  Ala  Gln  Lys  Glu
 1                  5                       10                      15

Ala  Glu  Lys  Lys  Ala  Ala  Glu  Glu  Lys  Lys  Ala  Lys  Glu  Ala  Glu  Ala
               20                       25                      30

Lys  Gln  Lys  Glu  Thr  Lys  Glu  Lys  Ser  Thr  Glu  Lys  Thr  Gly  Asp  Gly
          35                      40                      45

Gly  Ser  Ile  Gly  Lys  Asp  Lys  Asp  Val  Asp  Ala  Gly  Thr  Ser  Gly  Ser
     50                      55                      60

Val  Ser  Val  Pro  Lys  Leu  Lys  Ala  Met  Ser  Lys  Lys  Met  Arg  Leu  Pro
65                  70                      75                           80

Gln  Ala  Lys  Gly  Lys  Asn  Ile  Leu  His  Leu  Asp  Phe  Leu  Leu  Lys  Tyr
               85                      90                      95

Lys  Pro  Gln  Gln  Gln  Asp  Leu  Ser  Asn  Thr  Arg  Ala  Thr  Arg  Ala  Glu
               100                     105                     110

Phe  Asp  Arg  Trp  Tyr  Glu  Ala  Val  Gln  Lys  Glu  Tyr  Glu  Leu  Asp  Asp
          115                     120                     125

Thr  Gln  Met  Thr  Val  Val  Met  Ser  Gly  Leu  Met  Val  Trp  Cys  Ile  Glu
     130                     135                     140

Asn  Gly  Cys  Ser  Pro  Asn  Ile  Asn  Gly  Val  Trp  Thr  Met  Met  Asp  Gly
145                     150                     155                          160

Asp  Glu  Gln  Arg  Thr  Phe  Pro  Leu  Lys  Pro  Val  Ile  Glu  Asn  Ala  Ser
               165                     170                     175

Pro  Thr  Phe  Arg  Gln  Ile  Met  His  His  Phe  Ser  Asp  Ala  Ala  Glu  Ala
               180                     185                     190

Tyr  Ile  Glu  Tyr  Arg  Asn  Ser  Thr  Glu  Lys  Tyr  Met  Pro  Arg  Tyr  Ala
          195                     200                     205

Leu  Gln  Arg  Asn  Leu  Thr  Asp  Phe  Ser  Leu  Ala  Arg  Tyr  Ala  Phe  Asp
     210                     215                     220
```

```
Phe  Tyr  Glu  Ile  Ser  Ser  Arg  Thr  Pro  Val  Arg  Ala  Lys  Glu  Ala  His
225                      230                      235                      240

Met  Gln  Met  Lys  Ala  Ala  Ala  Val  Arg  Gly  Ser  Asn  Thr  Arg  Met  Phe
                    245                      250                      255

Gly  Leu  Asp  Gly  Asn  Val  Gly  Glu  Ala  His  Glu  Asn  Thr  Glu  Arg  His
                    260                      265                      270

Thr  Ala  Gly  Asp  Val  Ser  Pro  Asn  Met  His  Ser  Leu  Leu  Gly  Val  Gln
                    275                      280                      285

Gln  Gly  His
          290
```

(2) INFORMATION FOR SEQ ID NO:3:

(i) SEQUENCE CHARACTERISTICS:
        (A) LENGTH: 1221 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..987
        (D) OTHER INFORMATION: /codon_start=1

(xi) SEQUENCE DESCRIPTION: SEQ ID NO:3:

```
UCG  GGA  ACU  GUU  GAU  GCG  GGU  GCA  CAA  GGC  GGC  AGU  GGA  AGC  CAA  GGG         48
Ser  Gly  Thr  Val  Asp  Ala  Gly  Ala  Gln  Gly  Gly  Ser  Gly  Ser  Gln  Gly
 1                   5                        10                       15

ACA  ACA  CCA  CCA  GCA  ACA  GGU  AGU  GGA  GCA  AAA  CCA  GCC  ACC  UCA  GGG         96
Thr  Thr  Pro  Pro  Ala  Thr  Gly  Ser  Gly  Ala  Lys  Pro  Ala  Thr  Ser  Gly
               20                        25                       30

GCA  GGA  UCU  GGU  AGU  GGC  ACA  GGA  GCU  GGA  ACU  GGU  GUA  ACU  GGA  GGU        144
Ala  Gly  Ser  Gly  Ser  Gly  Thr  Gly  Ala  Gly  Thr  Gly  Val  Thr  Gly  Gly
               35                        40                       45

CAA  GCA  AGG  ACU  GGC  AGU  GGC  ACU  GGG  ACG  GGA  UCU  GGA  GCA  ACC  GGA        192
Gln  Ala  Arg  Thr  Gly  Ser  Gly  Thr  Gly  Thr  Gly  Ser  Gly  Ala  Thr  Gly
     50                        55                       60

GGC  CAA  UCA  GGA  UCU  GGA  AGU  GGC  ACU  GAA  CAG  GUU  AAC  ACG  GGU  UCA        240
Gly  Gln  Ser  Gly  Ser  Gly  Ser  Gly  Thr  Glu  Gln  Val  Asn  Thr  Gly  Ser
65                        70                       75                       80

GCA  GGA  ACU  AAU  GCA  ACU  GGA  GGC  CAA  AGA  GAU  AGG  GAU  GUG  GAU  GCA        288
Ala  Gly  Thr  Asn  Ala  Thr  Gly  Gly  Gln  Arg  Asp  Arg  Asp  Val  Asp  Ala
                    85                        90                       95

GGC  UCA  ACA  GGA  AAA  AUU  UCU  GUA  CCA  AAG  CUC  AAG  GCC  AUG  UCA  AAG        336
Gly  Ser  Thr  Gly  Lys  Ile  Ser  Val  Pro  Lys  Leu  Lys  Ala  Met  Ser  Lys
               100                      105                      110

AAA  AUG  CGC  UUA  CCU  AAA  GCA  AAA  GGA  AAA  GAU  GUG  CUA  CAU  UUG  GAU        384
Lys  Met  Arg  Leu  Pro  Lys  Ala  Lys  Gly  Lys  Asp  Val  Leu  His  Leu  Asp
          115                      120                      125

UUU  CUA  UUG  ACA  UAU  AAA  CCA  CAA  CAA  CAA  GAC  AUA  UCA  AAC  ACU  AGA        432
Phe  Leu  Leu  Thr  Tyr  Lys  Pro  Gln  Gln  Gln  Asp  Ile  Ser  Asn  Thr  Arg
     130                      135                      140

GCA  ACC  AAG  GAA  GAG  UUU  GAU  AGA  UGG  UAU  GAU  GCC  AUA  AAG  AAG  GAA        480
Ala  Thr  Lys  Glu  Glu  Phe  Asp  Arg  Trp  Tyr  Asp  Ala  Ile  Lys  Lys  Glu
145                      150                      155                      160

UAC  GAA  AUU  GAU  GAC  ACA  CAA  AUG  ACA  GUU  GUC  AUG  AGU  GGC  CUU  AUG        528
Tyr  Glu  Ile  Asp  Asp  Thr  Gln  Met  Thr  Val  Val  Met  Ser  Gly  Leu  Met
                    165                      170                      175

GUA  UGG  UGC  AUC  GAA  AAU  GGU  UGC  UCA  CCA  AAC  AUA  AAC  GGA  AAU  UGG        576
Val  Trp  Cys  Ile  Glu  Asn  Gly  Cys  Ser  Pro  Asn  Ile  Asn  Gly  Asn  Trp
                    180                      185                      190

ACA  AUG  AUG  GAU  AAA  GAU  GAA  CAA  AGG  GUC  UUC  CCA  CUC  AAA  CCG  GUC        624
```

| | | | | | | | | | | | | | | | |
|---|---|---|---|---|---|---|---|---|---|---|---|---|---|---|---|
| Thr | Met | Met | Asp | Lys | Asp | Glu | Gln | Arg | Val | Phe | Pro | Leu | Lys | Pro | Val |
| | | 195 | | | | 200 | | | | | | 205 | | | |

```
AUU GAG AAU GCA UCU CCA ACU UUC CGA CAA AUU AUG CAU CAU UUC AGU        672
Ile Glu Asn Ala Ser Pro Thr Phe Arg Gln Ile Met His His Phe Ser
    210             215                 220

GAU GCA GCU GAA GCG UAC AUA GAG UAC AGA AAC UCU ACU GAG CGA UAU        720
Asp Ala Ala Glu Ala Tyr Ile Glu Tyr Arg Asn Ser Thr Glu Arg Tyr
225             230                 235                 240

AUG CCA AGA UAC GGA CUU CAG CGC AAU AUC UCA GAC UAU AGC UUA GCA        768
Met Pro Arg Tyr Gly Leu Gln Arg Asn Ile Ser Asp Tyr Ser Leu Ala
            245                 250                 255

CGG UAU GCA UUU GAU UUC UAU GAA AUG ACU UCA CGC ACA CCU GCU AGA        816
Arg Tyr Ala Phe Asp Phe Tyr Glu Met Thr Ser Arg Thr Pro Ala Arg
        260                 265                 270

GCU AAA GAA GCC CAC AUG CAG AUG AAA GCC GCA GCA GUU CGU GGU UCC        864
Ala Lys Glu Ala His Met Gln Met Lys Ala Ala Ala Val Arg Gly Ser
    275                 280                 285

AAC ACA CGA CUG UUC GGU UUG GAC GGA AAU GUC GGC GAG ACU CAG GAG        912
Asn Thr Arg Leu Phe Gly Leu Asp Gly Asn Val Gly Glu Thr Gln Glu
    290             295                 300

AAU ACA GAG AGA CAC ACA GCU GGC GAU GUU AGU CGC AAC AUG CAC UCU        960
Asn Thr Glu Arg His Thr Ala Gly Asp Val Ser Arg Asn Met His Ser
305             310                 315                 320

CUG UUG GGA GUG CAG CAA CAC CAC UAGUCCCUG GAAACCCUGU UUGCAGUACC       1014
Leu Leu Gly Val Gln Gln His His
            325

AAUAAUAUGU ACUAAUAUAU AGUAUUUUAG UGAGGUUUUA CCUCGUCUUU ACUGUUUUAU     1074

UACGUAUGUA UUUAAAGCGU GAACCAGUCU GCAACAUACA GGGUUGGACC CAGUGUGUUC     1134

UGGUGUAGCG UGUACUAGCG UCGAGCCAUG AGAUGGACUG CACUGGGUGU GGUUUUGCCA     1194

CUUGUGUUGC GAGUCUCUGG UAAGAGA                                        1221
```

( 2 ) INFORMATION FOR SEQ ID NO:4:

( i ) SEQUENCE CHARACTERISTICS:
        ( A ) LENGTH: 328 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Ser Gly Thr Val Asp Ala Gly Ala Gln Gly Gly Ser Gly Ser Gln Gly
 1               5                   10                  15

Thr Thr Pro Pro Ala Thr Gly Ser Gly Ala Lys Pro Ala Thr Ser Gly
            20                  25                  30

Ala Gly Ser Gly Ser Gly Thr Gly Ala Gly Thr Gly Val Thr Gly Gly
        35                  40                  45

Gln Ala Arg Thr Gly Ser Gly Thr Gly Thr Gly Ser Gly Ala Thr Gly
    50                  55                  60

Gly Gln Ser Gly Ser Gly Ser Gly Thr Glu Gln Val Asn Thr Gly Ser
65                  70                  75                  80

Ala Gly Thr Asn Ala Thr Gly Gly Gln Arg Asp Arg Asp Val Asp Ala
                85                  90                  95

Gly Ser Thr Gly Lys Ile Ser Val Pro Lys Leu Lys Ala Met Ser Lys
            100                 105                 110

Lys Met Arg Leu Pro Lys Ala Lys Gly Lys Asp Val Leu His Leu Asp
        115                 120                 125

Phe Leu Leu Thr Tyr Lys Pro Gln Gln Gln Asp Ile Ser Asn Thr Arg
```

|     | 130 |     |     |     | 135 |     |     |     | 140 |     |     |     |     |
| --- | --- | --- | --- | --- | --- | --- | --- | --- | --- | --- | --- | --- | --- |

Ala Thr Lys Glu Glu Phe Asp Arg Trp Tyr Asp Ala Ile Lys Lys Glu
145                     150                 155                 160

Tyr Glu Ile Asp Asp Thr Gln Met Thr Val Val Met Ser Gly Leu Met
                165                 170                 175

Val Trp Cys Ile Glu Asn Gly Cys Ser Pro Asn Ile Asn Gly Asn Trp
            180                 185                 190

Thr Met Met Asp Lys Asp Glu Gln Arg Val Phe Pro Leu Lys Pro Val
        195                 200                 205

Ile Glu Asn Ala Ser Pro Thr Phe Arg Gln Ile Met His His Phe Ser
    210                 215                 220

Asp Ala Ala Glu Ala Tyr Ile Glu Tyr Arg Asn Ser Thr Glu Arg Tyr
225                 230                 235                 240

Met Pro Arg Tyr Gly Leu Gln Arg Asn Ile Ser Asp Tyr Ser Leu Ala
                245                 250                 255

Arg Tyr Ala Phe Asp Phe Tyr Glu Met Thr Ser Arg Thr Pro Ala Arg
            260                 265                 270

Ala Lys Glu Ala His Met Gln Met Lys Ala Ala Ala Val Arg Gly Ser
        275                 280                 285

Asn Thr Arg Leu Phe Gly Leu Asp Gly Asn Val Gly Glu Thr Gln Glu
    290                 295                 300

Asn Thr Glu Arg His Thr Ala Gly Asp Val Ser Arg Asn Met His Ser
305                 310                 315                 320

Leu Leu Gly Val Gln Gln His His
                325

( 2 ) INFORMATION FOR SEQ ID NO:5:

( i ) SEQUENCE CHARACTERISTICS:
    ( A ) LENGTH: 1385 base pairs
    ( B ) TYPE: nucleic acid
    ( C ) STRANDEDNESS: single
    ( D ) TOPOLOGY: linear ( i x ) FEATURE:
    ( A ) NAME/KEY: CDS
    ( B ) LOCATION: 1..909
    ( D ) OTHER INFORMATION: /codon_start=1

( x i ) SEQUENCE DESCRIPTION: SEQ ID NO:5:

```
UCA GGC AAU GAA GAU GCU GGA AGA CAG AAG AGU GCG GCA CCA GCU GAA        48
Ser Gly Asn Glu Asp Ala Gly Arg Gln Lys Ser Ala Ala Pro Ala Glu
 1               5                  10                  15

AAC AAA CCA GCU AGU GGU GAA GGC AAA CCA GCA CAA ACG ACA GCG ACA        96
Asn Lys Pro Ala Ser Gly Glu Gly Lys Pro Ala Gln Thr Thr Ala Thr
             20                  25                  30

UCA GAC AAC AAA CCA UCC UCU GAU AAC ACU UCG AAU ACU CAA GGA ACA       144
Ser Asp Asn Lys Pro Ser Ser Asp Asn Thr Ser Asn Thr Gln Gly Thr
         35                  40                  45

UCA CAA GCC AAA GGA GAU AGU GAA UCA GGU GGA ACA AAG GCC UCA ACG       192
Ser Gln Ala Lys Gly Asp Ser Glu Ser Gly Gly Thr Lys Ala Ser Thr
     50                  55                  60

GCA ACG AAA GAC AAG GAU GUC GAC GUU GGA UCA ACC GGA ACU UUU GUU       240
Ala Thr Lys Asp Lys Asp Val Asp Val Gly Ser Thr Gly Thr Phe Val
 65                  70                  75                  80

AUU CCG AAA UUG AAG AAG GUU UCG CCC AAG AUG CGU CUA CCC AUG GUG       288
Ile Pro Lys Leu Lys Lys Val Ser Pro Lys Met Arg Leu Pro Met Val
                 85                  90                  95

AGC AAC AAA GCC AUA CUC AAC CUG GAU CAU UUA AUC CAG UAC AAG CCA       336
Ser Asn Lys Ala Ile Leu Asn Leu Asp His Leu Ile Gln Tyr Lys Pro
```

|  |  | 100 |  |  |  | 105 |  |  |  | 110 |  |  |  |  |
|---|---|---|---|---|---|---|---|---|---|---|---|---|---|---|
| GAC | CAG | AGA | GAU | AUC | UCG | AAC | GCU | CGU | GCC | ACA | CAC | ACA | CAA | UUC | CAA | 384 |
| Asp | Gln | Arg | Asp | Ile | Ser | Asn | Ala | Arg | Ala | Thr | His | Thr | Gln | Phe | Gln |
|  |  | 115 |  |  |  | 120 |  |  |  | 125 |  |  |  |  |
| UUC | UGG | UAC | AAC | AGA | AUU | AAG | AAG | GAA | UAC | GAC | GUU | GAU | GAC | GAG | CAA | 432 |
| Phe | Trp | Tyr | Asn | Arg | Ile | Lys | Lys | Glu | Tyr | Asp | Val | Asp | Asp | Glu | Gln |
|  | 130 |  |  |  | 135 |  |  |  | 140 |  |  |  |  |  |
| AUG | AGG | AUC | UUG | AUG | AAC | GGA | UUA | AUG | GUC | UGG | UGU | AUA | GAG | AAU | GGC | 480 |
| Met | Arg | Ile | Leu | Met | Asn | Gly | Leu | Met | Val | Trp | Cys | Ile | Glu | Asn | Gly |
| 145 |  |  |  | 150 |  |  |  | 155 |  |  |  |  |  | 160 |
| ACA | UCU | CCU | GAU | AUA | AAU | GGU | UAC | UGG | ACC | AUG | GUG | GAU | GGA | AAC | AAU | 528 |
| Thr | Ser | Pro | Asp | Ile | Asn | Gly | Tyr | Trp | Thr | Met | Val | Asp | Gly | Asn | Asn |
|  |  |  |  | 165 |  |  |  | 170 |  |  |  | 175 |
| CAA | UCU | GAA | UUU | CCA | CUA | AAG | CCA | AUA | GUG | GAA | AAU | GCA | AAA | CCA | ACA | 576 |
| Gln | Ser | Glu | Phe | Pro | Leu | Lys | Pro | Ile | Val | Glu | Asn | Ala | Lys | Pro | Thr |
|  |  |  | 180 |  |  |  | 185 |  |  |  | 190 |
| UUA | CGA | CAG | UGC | AUG | AUG | CAU | UUU | AGU | GAC | GCC | GCA | GAA | GCG | UAC | AUU | 624 |
| Leu | Arg | Gln | Cys | Met | Met | His | Phe | Ser | Asp | Ala | Ala | Glu | Ala | Tyr | Ile |
|  |  | 195 |  |  |  | 200 |  |  |  | 205 |
| GAA | AUG | AGA | AAU | UUG | GAU | GAG | CCG | UAC | AUG | CCA | AGA | UAC | GGU | CUC | CUU | 672 |
| Glu | Met | Arg | Asn | Leu | Asp | Glu | Pro | Tyr | Met | Pro | Arg | Tyr | Gly | Leu | Leu |
| 210 |  |  |  | 215 |  |  |  | 220 |
| AGG | AAU | CUA | AAU | GAC | AAG | AGC | CUC | GCU | CGA | UAC | GCA | UUU | GAU | UUC | UAU | 720 |
| Arg | Asn | Leu | Asn | Asp | Lys | Ser | Leu | Ala | Arg | Tyr | Ala | Phe | Asp | Phe | Tyr |
| 225 |  |  |  | 230 |  |  |  | 235 |  |  |  |  |  | 240 |
| GAG | AUC | AAU | UCG | CGC | ACG | CCA | AAU | AGA | GCG | AGA | GAG | GCA | CAU | GCA | CAA | 768 |
| Glu | Ile | Asn | Ser | Arg | Thr | Pro | Asn | Arg | Ala | Arg | Glu | Ala | His | Ala | Gln |
|  |  |  | 245 |  |  |  | 250 |  |  |  | 255 |
| AUG | AAG | GCA | GCA | GCA | AUU | AGA | GGG | UCU | ACG | AAC | CAC | AUG | UUU | GGA | CUC | 816 |
| Met | Lys | Ala | Ala | Ala | Ile | Arg | Gly | Ser | Thr | Asn | His | Met | Phe | Gly | Leu |
|  |  | 260 |  |  |  | 265 |  |  |  | 270 |
| GAC | GGG | AAU | GUU | GGA | GAG | AGC | UCU | GAG | AAU | ACA | GAG | CGG | CAC | ACA | GCU | 864 |
| Asp | Gly | Asn | Val | Gly | Glu | Ser | Ser | Glu | Asn | Thr | Glu | Arg | His | Thr | Ala |
|  |  | 275 |  |  |  | 280 |  |  |  | 285 |
| GCA | GAU | GUC | UCA | CGG | AAU | GUC | CAU | UCG | UAC | CGU | GGG | GCC | AAA | AUC |  | 909 |
| Ala | Asp | Val | Ser | Arg | Asn | Val | His | Ser | Tyr | Arg | Gly | Ala | Lys | Ile |
|  | 290 |  |  |  | 295 |  |  |  | 300 |

```
UAAGGAGGAG GAACAACCGU CUAUCUGACG UUAAGGAUG ACUGGCCAAG UCUGAAAAUU      969
GGCGUGAUAC CAGUUCCGAA UAGUCCAUAC AGAAUUAGAG GUGAACAGAG AGCACUAUAA    1029
AGGUUUAGUA GGGAUCGAGA GAUGACACGU AGGACCUCAA UGACCAUGCU UAGCGCUAGC    1089
AUUGUGUGGA GCUCUAACAC UCAGGUGUUA UCUUCCAGGC UGUGGUAAUC UCGUACCCCG    1149
AAGUACCUAU GGGCCCUCAG CACCAGACAG UACUGGGACU AUGUAUCCUU UCUUGGCAAU    1209
CACUAGUAUU AUAAAUCGUU CUGCAACGGC ACGAGUGGUG UUUUACACCU GGGUGGAAUC    1269
CUAAUGCUGU UAUACAGUUA UGGAUAACGG CCCGUGUUGU UCGUAUUUAC UAGUUGCAUC    1329
AGACCAUCUG AGCCUCAGAG UGAGCUUCUC ACCACGCAGU CUCUUAUGGC GAGAUA        1385
```

( 2 ) INFORMATION FOR SEQ ID NO:6:

( i ) SEQUENCE CHARACTERISTICS:
            ( A ) LENGTH: 303 amino acids
            ( B ) TYPE: amino acid
            ( D ) TOPOLOGY: linear ( i i ) MOLECULE TYPE: protein ( x i ) SEQUENCE DESCRIPTION: SEQ ID NO:6:

| Ser | Gly | Asn | Glu | Asp | Ala | Gly | Arg | Gln | Lys | Ser | Ala | Ala | Pro | Ala | Glu |
|---|---|---|---|---|---|---|---|---|---|---|---|---|---|---|---|
| 1 |  |  |  | 5 |  |  |  |  | 10 |  |  |  |  | 15 |

| | | | | | | | | | | | | | |
|---|---|---|---|---|---|---|---|---|---|---|---|---|---|
| Asn | Lys | Pro | Ala<br>20 | Ser | Gly | Glu | Gly | Lys<br>25 | Pro | Ala | Gln | Thr<br>30 | Thr | Ala | Thr |
| Ser | Asp | Asn<br>35 | Lys | Pro | Ser | Ser | Asp<br>40 | Asn | Thr | Ser | Asn | Thr<br>45 | Gln | Gly | Thr |
| Ser | Gln<br>50 | Ala | Lys | Gly | Asp | Ser<br>55 | Glu | Ser | Gly | Gly | Thr<br>60 | Lys | Ala | Ser | Thr |
| Ala | Thr<br>65 | Lys | Asp | Lys | Asp<br>70 | Val | Asp | Val | Gly | Ser<br>75 | Thr | Gly | Thr | Phe | Val<br>80 |
| Ile | Pro | Lys | Leu | Lys<br>85 | Lys | Val | Ser | Pro | Lys<br>90 | Met | Arg | Leu | Pro | Met<br>95 | Val |
| Ser | Asn | Lys | Ala<br>100 | Ile | Leu | Asn | Leu | Asp<br>105 | His | Leu | Ile | Gln | Tyr<br>110 | Lys | Pro |
| Asp | Gln | Arg<br>115 | Asp | Ile | Ser | Asn | Ala<br>120 | Arg | Ala | Thr | His | Thr<br>125 | Gln | Phe | Gln |
| Phe | Trp<br>130 | Tyr | Asn | Arg | Ile | Lys<br>135 | Lys | Glu | Tyr | Asp | Val<br>140 | Asp | Asp | Glu | Gln |
| Met<br>145 | Arg | Ile | Leu | Met | Asn<br>150 | Gly | Leu | Met | Val | Trp<br>155 | Cys | Ile | Glu | Asn | Gly<br>160 |
| Thr | Ser | Pro | Asp | Ile<br>165 | Asn | Gly | Tyr | Trp | Thr<br>170 | Met | Val | Asp | Gly | Asn<br>175 | Asn |
| Gln | Ser | Glu | Phe<br>180 | Pro | Leu | Lys | Pro | Ile<br>185 | Val | Glu | Asn | Ala | Lys<br>190 | Pro | Thr |
| Leu | Arg | Gln<br>195 | Cys | Met | Met | His | Phe<br>200 | Ser | Asp | Ala | Ala | Glu<br>205 | Ala | Tyr | Ile |
| Glu | Met<br>210 | Arg | Asn | Leu | Asp | Glu<br>215 | Pro | Tyr | Met | Pro | Arg<br>220 | Tyr | Gly | Leu | Leu |
| Arg<br>225 | Asn | Leu | Asn | Asp | Lys<br>230 | Ser | Leu | Ala | Arg | Tyr<br>235 | Ala | Phe | Asp | Phe | Tyr<br>240 |
| Glu | Ile | Asn | Ser | Arg<br>245 | Thr | Pro | Asn | Arg | Ala<br>250 | Arg | Glu | Ala | His | Ala<br>255 | Gln |
| Met | Lys | Ala | Ala<br>260 | Ala | Ile | Arg | Gly | Ser<br>265 | Thr | Asn | His | Met | Phe<br>270 | Gly | Leu |
| Asp | Gly | Asn<br>275 | Val | Gly | Glu | Ser | Ser<br>280 | Glu | Asn | Thr | Glu | Arg<br>285 | His | Thr | Ala |
| Ala | Asp<br>290 | Val | Ser | Arg | Asn | Val<br>295 | His | Ser | Tyr | Arg | Gly<br>300 | Ala | Lys | Ile |

( 2 ) INFORMATION FOR SEQ ID NO:7:

( i ) SEQUENCE CHARACTERISTICS:
  ( A ) LENGTH: 5 amino acids
  ( B ) TYPE: amino acid
  ( C ) STRANDEDNESS: unknown
  ( D ) TOPOLOGY: linear ( x i ) SEQUENCE DESCRIPTION: SEQ ID NO:7:

Trp Cys Ile Glu Asn
1          5

( 2 ) INFORMATION FOR SEQ ID NO:8:

( i ) SEQUENCE CHARACTERISTICS:
  ( A ) LENGTH: 12 base pairs
  ( B ) TYPE: nucleic acid
  ( C ) STRANDEDNESS: single
  ( D ) TOPOLOGY: linear ( i x ) FEATURE:
  ( A ) NAME/KEY: CDS ( B ) LOCATION: 1..12
            ( D ) OTHER INFORMATION: /codon_start=1

( x i ) SEQUENCE DESCRIPTION: SEQ ID NO:8:

CAG TCG GGA ACT                                                                         12
Gln Ser Gly Thr
  1

( 2 ) INFORMATION FOR SEQ ID NO:9:

( i ) SEQUENCE CHARACTERISTICS:
            ( A ) LENGTH: 4 amino acids
            ( B ) TYPE: amino acid
            ( D ) TOPOLOGY: linear ( i i ) MOLECULE TYPE: protein ( x i ) SEQUENCE DESCRIPTION: SEQ ID NO:9:

Gln Ser Gly Thr
  1

( 2 ) INFORMATION FOR SEQ ID NO:10:

( i ) SEQUENCE CHARACTERISTICS:
            ( A ) LENGTH: 12 base pairs
            ( B ) TYPE: nucleic acid
            ( C ) STRANDEDNESS: unknown
            ( D ) TOPOLOGY: linear ( i x ) FEATURE:
            ( A ) NAME/KEY: CDS
            ( B ) LOCATION: 1..12
            ( D ) OTHER INFORMATION: /codon_start=1

( x i ) SEQUENCE DESCRIPTION: SEQ ID NO:10:

CAG TCG GGT ACC                                                                         12
Gln Ser Gly Thr
  1

( 2 ) INFORMATION FOR SEQ ID NO:11:

( i ) SEQUENCE CHARACTERISTICS:
            ( A ) LENGTH: 4 amino acids
            ( B ) TYPE: amino acid
            ( D ) TOPOLOGY: linear ( i i ) MOLECULE TYPE: protein ( x i ) SEQUENCE DESCRIPTION: SEQ ID NO:11:

Gln Ser Gly Thr
  1

( 2 ) INFORMATION FOR SEQ ID NO:12:

( i ) SEQUENCE CHARACTERISTICS:
            ( A ) LENGTH: 12 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:12:

CTAGTCTGCA GA                                                                           12

( 2 ) INFORMATION FOR SEQ ID NO:13:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: linear -continued ( x i ) SEQUENCE DESCRIPTION: SEQ ID NO:13:

CTAGAGTCGA CCATGTCGGG 20

( 2 ) INFORMATION FOR SEQ ID NO:14:

( i ) SEQUENCE CHARACTERISTICS:
( A ) LENGTH: 19 base pairs
( B ) TYPE: nucleic acid
( C ) STRANDEDNESS: single
( D ) TOPOLOGY: linear ( x i ) SEQUENCE DESCRIPTION: SEQ ID NO:14:

GTACCCGACA TGGTCGACT 19

( 2 ) INFORMATION FOR SEQ ID NO:15:

( i ) SEQUENCE CHARACTERISTICS:
( A ) LENGTH: 40 base pairs
( B ) TYPE: nucleic acid
( C ) STRANDEDNESS: single
( D ) TOPOLOGY: linear ( x i ) SEQUENCE DESCRIPTION: SEQ ID NO:15:

CTCAAGCTTT CTAGAGTCGA CCATGTCAGG CAATGAAGAT 40

( 2 ) INFORMATION FOR SEQ ID NO:16:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( x i ) SEQUENCE DESCRIPTION: SEQ ID NO:16:

GCACCCCGGT TTTAGATTAC GTACGAG 27